(12) United States Patent
Ma et al.

(10) Patent No.: US 9,476,879 B2
(45) Date of Patent: Oct. 25, 2016

(54) TEST STRIP DETECTION SYSTEM

(71) Applicant: Chengdu Lingyu Biotechnology Co., Ltd., Chengdu, Sichuan (CN)

(72) Inventors: Yicai Ma, Chengdu (CN); Min Gu, Chengdu (CN); Ling Ma, Chengdu (CN)

(73) Assignee: CHENGDU LINGYU BIOTECHNOLOGY CO., LTD. (CN)

( * ) Notice: Subject to any disclaimer, the term of this patent is extended or adjusted under 35 U.S.C. 154(b) by 0 days.

(21) Appl. No.: 14/355,414

(22) PCT Filed: Oct. 30, 2012

(86) PCT No.: PCT/CN2012/083719
§ 371 (c)(1),
(2) Date: Apr. 30, 2014

(87) PCT Pub. No.: WO2013/064054
PCT Pub. Date: May 10, 2013

(65) Prior Publication Data
US 2014/0273189 A1  Sep. 18, 2014

(30) Foreign Application Priority Data

Nov. 1, 2011 (CN) .......................... 2011 1 0338294

(51) Int. Cl.
G01N 33/00 (2006.01)
G01N 33/569 (2006.01)
G01J 3/02 (2006.01)
G01J 3/42 (2006.01)
G01N 21/84 (2006.01)

(52) U.S. Cl.
CPC ....... *G01N 33/56983* (2013.01); *G01J 3/0208* (2013.01); *G01J 3/0218* (2013.01); *G01J 3/0264* (2013.01); *G01J 3/0272* (2013.01); *G01J 3/0283* (2013.01); *G01J 3/0291* (2013.01); *G01J 3/42* (2013.01); *G01N 21/8483* (2013.01)

(58) Field of Classification Search
CPC . G01N 33/56983; G01N 3/283; G01N 3/208
See application file for complete search history.

(56) References Cited

U.S. PATENT DOCUMENTS 4,476,149 A  10/1984  Poppe et al.
2012/0262716 A1  10/2012  Wang et al.

FOREIGN PATENT DOCUMENTS

| CN | 1536522 A | 10/2004 |
|---|---|---|
| CN | 101578519 A | 11/2009 |
| CN | 101769925 A | 7/2010 |
| WO | WO-2010120951 A1 | 10/2010 |
| WO | WO-2011076013 A1 | 6/2011 |

OTHER PUBLICATIONS

International Search Report and Written Opinion issued by the State Intellectual Property Office of China for International Application No. PCT/CN2012/083719 mailed Feb. 7, 2013 (21 pgs.)

*Primary Examiner* — Sam P Siefke
(74) *Attorney, Agent, or Firm* — Wilmer Cutler Pickering Hale and Dorr LLP

(57) ABSTRACT

A test strip detection system, comprising a test strip card (1) and a detection device (2); the test strip card (1) comprises a card box (16), a built-in test strip (15) and an electronic label (20) matched with the built-in test strip (15); the electronic label (20) stores parameters such as the standard working curve of an object to be detected and the like; the detection device (2) comprises an optical system (3), a photoelectric detector (4), an analog/digital converter (5), a data processing device (6), an electronic label read-write module (10) with an aerial (11), a voice module (34), a cell box (7) and an output display device (8). The system further comprises a wireless communication module (12) and a wireless network system (13) connected with the wireless communication module (12) and comprising a remote server (14). The data processing device (6) calculates a sample detection result according to the characteristic frequency optical signals transmitted by a test strip detection band (27) and a quality control band (28) in combination with an electronic label (20) transmission parameter; the detection result is displayed on the output display device (8); the voice module (34) vocally prompts the detection result at the same time; the detection result is transmitted to the remote server (14) via the wireless communication module (12) for data management and information feedback.

20 Claims, 9 Drawing Sheets

TEST STRIP DETECTION SYSTEM

CROSS REFERENCE TO RELATED APPLICATIONS

This application is a National Stage Entry of PCT/CN2012/083719 filed on Oct. 30, 2012, which claims priority to Chinese Application No. 201110338294.5 filed on Nov. 1, 2011, the contents of which are hereby incorporated by reference in their entirety.

FIELD OF THE INVENTION

The present invention relates to the field of biomedical appliances, and in particular, to a test strip testing system. The test strip testing system is operable to automatically scan and detect a test strip on which a substance to be detected is applied and interpret a testing result, thereby realizing the quantitative detection of various detected substance such as pathogen, antigen, antibody, banned drug, dread disease (tumour, cancer, cardiovascular disease, diabetes, etc.), pesticide residue, food security biological detection, etc., and sending the testing result and the related information to a remote server for management and information consultation feedback.

BACKGROUND OF THE INVENTION

At present, biomedical diagnosis and detection products generally develop rapidly toward two directions, i.e., a development direction toward highly integrated and automatized large-scale products and a development direction toward simple, rapid and easily popularized mini portable products. However, no matter for large-scale apparatus, medium-scale apparatus or mini portable microminiaturized products, there is always a need to realize synchronous quantitative detection, especially synchronous rapid quantitative detection, of multiple components of a sample.

An immunochromatographic test strip is an immunolabeling technology developed on the basis of enzyme linked immunosorbent assay (ELISA), and is used to conveniently and rapidly test a sample, and the testing result can be obtained in a few minutes, and hence is referred to as "concentrated ELISA". A colloidal gold test strip is one of the most common technologies, and is now widely used in almost all aspects of biomedical rapid detection. However, it has the following disadvantages: 1) a sample can only be rapidly detected qualitatively via a colloidal gold test strip, and no quantitative detection of a sample can be realized, thus it is generally used only for the primary screening testing of a sample, and no validation report of the testing result can be provided, therefore, the clinical application range thereof and the detection effect evaluation thereof are limited; and 2) generally, only one sample index can be tested by one test strip, so it is difficult to realize simultaneous test of multiple indexes of a sample, resulting in a low testing efficiency.

Radio Frequency Identification (RFD) is a non-contact automatic identification technology emerged in 1990s. An RFID tag has a small volume but with a large information storage capacity, its operation is simple and convenient because manual intervention is not required for identification, and is cheap, thus the RFID has been widely used in various fields such as industry, business, traffic control and management, etc. However, the RFID is seldom used for a biomedical sample test. An RFID system for colloidal gold immunochromatographic test was designed by Jian WANG (see Research on the application of RFID technology in colloidal gold immunochromatography by Jian WANG, 2007: 96-100). However, it has the following disadvantages: 1) the test system with an RFID read and write function, which is described in this design, is only directed to a colloidal gold test strip, and the system is consisted of a radio-frequency card reading module, a radio frequency label and a mastercontrol monolithic processor, but the solving of the important problem as to how the system specifically realizes the quantitative detection of a sample via a colloidal gold test strip is not involved; 2) it is difficult for a colloidal gold test strip to realize the simultaneous detection of multiple indexes of a sample; and 3) the test strip card of this design has a complex structure and its manufacturing is difficult and expensive, and the detection fee bearing capability of a subject subjected to the sample testing is not considered. At present, the test strip is fixed in the card box of the test strip card and cannot be replaced flexibly as desired depending on different samples, and the subject that is subjected to the sample testing has to bear an unnecessary cost for the test strip card box carrying the test strip, so that the economic burden of the subject is increased. Chinese Patent Application No. 200910044926.X and Chinese Patent No. ZL200920066534.9 disclose a radio frequency identification card installed on the envelope of a phosphorescent test paper strip, and provide a method for calculating sample concentrations, where a parameter A, a parameter B and a threshold value used for detection, which are related to the method for calculating sample concentrations, are also stored on the radio frequency identification card. However, it has the following disadvantages: 1) the information stored on the radio frequency identification card is not a standard curve of a substance be detected, and for the quantitative detection of a sample, it will be simpler, more convenient and more accurate when a standard curve of the substance to be detected is stored; and 2) in these two patents/patent applications, the detection fee bearing capability of a subject that is subjected to the sample testing is still not considered synthetically from the structure of the test paper strip. By the structure of the test paper strip, the built-in test paper still cannot be replaced flexibly as desired depending on different samples. If a test paper strip envelope can be shared continuously by test papers of the same batch and at the same time, a radio frequency identification card for the quantification of test papers of the same batch is installed on the envelope, not only the production cost of the test paper strip structure can be saved, and the parameter storing and manufacturing process of the radio frequency identification card can be reduced, but also a sample test can be made economical, flexible and convenient (only the built-in test paper is replaced for different samples each time a detection is performed), the cost of the test paper strip envelope unnecessarily paid by the subject that is subjected to the sample testing can be lowered, and it is convenient and meets the requirement that in vitro diagnosis and detection products should be inspected for every batch when leaving the factory. The solutions described in the document by Wang Jian, Patent Application No. 200910044926.X and Patent No. ZL200920066534.9 all have such a problem, and remote data management on the testing result of a sample and rapid and accurate polycomponent quantification of a sample cannot be realized in the above patents. Additionally, Patent Application No. 200580003180.8 discloses an immune test strip system in which an RFID tag and a sensor module are combined on a substrate. However, it has the following disadvantages: the solution of the problem how the quantitative detection of a sample is realized is still not described in the immune test strip system, and the structural composition of thee wireless radio frequency identification sensor is totally different from that of the invention.

In view of the above shortages of the prior art, the invention discloses a test strip testing system, in which not only test strips can be replaced depending on the detection requirements, but also the rapid and accurate quantitative testing (including on-site rapid quantitative testing) of a sample can be realized in a few minutes without other equipments or reagents; moreover, the dynamic procedure of the immunochromatographic reaction can be observed, and the testing result information can be transmitted to a remote server instantly for management and information consultation feedback. When a test strip on which a sample to be tested is applied is a quantum dot-marked test strip, the system of the invention can also realize a rapid and accurate simultaneous quantitative detection of multiple components in a sample.

SUMMARY OF THE INVENTION

An aspect of the present invention is to provide a test strip testing system, which not only can realize monocomponent or polycomponent quantitative detection (as well as qualitative detection) of a detected substance, but also can observe the dynamic procedure of the immunochromatographic reaction. In detecting a sample, the system of the invention is advantageous by convenient and rapid detection, high sensitivity, objective testing result, and flexible usage.

The above object of the invention is realized by the following technical solutions. A test strip testing system includes a test strip card 1 and a testing device 2. The test strip card 1 includes a test strip card box 16, a test strip 15 inserted into the test strip card box 16, and an electronic tag 20 that is installed on the card box 16 and configured to store test strip information. The testing device 2 includes an optical system 3, a photoelectric detector 4, an analog-to-digital converter 5, a data processor 6, an electronic tag reading and writing module 10 with an antenna 11, a voice module 34, a cell box 7, an output display means 8, and a plurality of keys 9 and a plurality of communication interfaces 31 located on the surface of the testing device 2.

The test strip card 1 is configured to be inserted into the testing device 2. The test strip 15 is configured to be inserted into the test strip card 1. The front end of the testing device 2 is provided with a test strip card receptacle 33, which is configured to receive the test strip card 1 inserted with a test strip 15, for detecting a sample on the test strip.

The electronic tag 20 may be, but is not limited to, an RFID tag or a non-contact identification IC card, and installed anywhere in the test strip card box 16 in a film bonding, encapsulating and implanting, clamping, pinning or snapping manner. The electronic tag 20 stores a standard curve for the detection of a substance using test strips of the same batch for quantifying a sample concentration, or stores both a standard curve for the detection of a substance using test strips of the same batch for quantifying a sample concentration and a reference optical density value ($OD_{control\ line'}$) of the test strip control line, and the electronic tag 20 stores the numerical value of a characteristic wavelength of the excited light and/or the numerical value of a characteristic wavelength of the reflected light, for the detection of the detected substance, and stores the test strip information including a test strip batch number, test strip expiration date, electronic tag cryptogram, a reference value of a clinical index, test strip manufacturer information, etc.; moreover, information such as identity information of the tested object, tester cryptogram, a sample name, a sample sequence number, test date and a test result is writable into the electronic tag 20. The electronic tag 20 may store various forms of standard curves, which include, but are not limited to, one from a group including: a correspondence curve between the series concentration of the standard product of the detected substance and $OD_{test\ line}/OD_{control\ line}$, and a correspondence curve between the series concentration of the standard product of the detected substance and $OD_{test\ line}/(OD_{test\ line}+OD_{control\ line})$. Herein, $OD_{test\ line}$ denotes the optical density value of the test line detected for the series concentration of the standard product of the detected substance, and $OD_{control\ line}$ denotes the optical density value of the control line detected for the series concentration of the standard product of the detected substance.

The test strip 15 inserted into the test strip card 1 includes a sample pad 21, a glass fiber film binding pad 22 coated with a marker, an analysis membrane 23 with a test line 27 and a control line 28, a super-absorbent pad 24 and a test strip reaction end position indication label 25, which are sequentially overlapped with one another and stuck mutually. The test strip 15 inserted into the test strip card 1 may be any test strip, which includes, but is not limited to, quantum dot-marked test strip, colloidal gold-marked test strip, colloidal selenium-marked test strip, upconversion phosphorescence-marked test strip, nano rare earth fluorescent complex-marked test strip, temporal resolution chromatography test strip, chemiluminescence test strip, or other test strips.

The test strip card box 16 of the test strip card 1 has an opening end 17 for receiving the test strip 15 as desired during the sample test. The upper side of the opening end 17 of the test strip card box has a notch 18 for easily inserting the test strip 15 into the test strip card box 16. A sample absorption end of the test strip 15 (i.e., the sample pad 21) that is inserted into the card box 16 extends out of the open end 17 of the test strip card box so as to allow the test strip 15 to dip into and absorb a sample. The upper side of the test strip card box 16 is provided with a verification window 29 at a location corresponding to the test line and the control line of the test strip in the card box, and is provided with a test strip reaction end position observation window 30 at a location corresponding to the reaction end position indication label 25 of the test strip in the card box. A test strip card insertion stop flag 19 is provided on the surface of the test strip card 1 at a location corresponding to the test strip card receptacle 33 of the testing device 2.

An imaging signal terminal of the optical system 3 is connected with the photoelectric detector 4. The optical system 3 has such a diversified structure (but is not limited to) that:

1) the optical system 3 includes an illuminating system and an imaging system, where the illuminating system includes an exciting light source 311, and an optical fiber bundle 312, a collimating lens 313, a dichroic mirror 314, a front lens group 315 form an output light path from the light source 311 to the test strip card 1. The exciting light source 311 includes a light-emitting diode (LED) or a laser diode. The imaging system includes a front lens group 315, a dichroic mirror 314, a filter plate 316 and a rear lens group 317 that are arranged coaxially, wherein an included angle 45° is formed between a reflecting surface of the dichroic mirror 314 and the optical axis, the front lens group 315 and the rear lens group 317 both employ an isolated structure, a light path of the illuminating system before the dichroic mirror 314 is vertical to the optical axis of the imaging system, and a light path of the illuminating system after the dichroic mirror 314 is coaxial with the imaging system; the photoelectric detector 4 is located on an image plane of the rear lens group 317; the optical fiber bundle 312 is configured to divide the light emitted by the light source 311 into two laser beams with the same intensity that are spaced apart from each other, and these two laser beams are collimated by the collimating lens 313 into two parallel light beams which irradiate on the surface of the dichroic mirror 314, and synchronously irradiate on the test line 27 and the control line 28 of the test strip 15 in the test strip card 1 that are located in an object plane of the front lens group 315 via the front lens group 315 after being reflected by the dichroic mirror 314, to excite the test strip reaction signifier that permeates to the test line 27 and the control line 28 to emit reflected light with a characteristic frequency, the reflected light from the test line 27 and the control line 28 passes through the same front lens group 315 and the dichroic mirror 314, is filtered by the filter plate 316 to filter out parasitic light, exits from the rear lens group 317, and then enters into the photoelectric detector 4 to be detected and converted into an electrical signal by the photoelectric detector 4; or 2) the optical system 3 includes an exciting light source 321, and an incident light coupler 322, incident light optical fibers 3231 and 3232, optical fiber probes 3241 and 3242, emergent light optical fibers 3251 and 3252 and emergent light couplers 3261 and 3262 form an output light path from the exciting light source 321 to the photoelectric detector 4; the exciting light source 321 includes a light-emitting diode (LED) or a laser diode; the light emitted by the light source 321 is divided into two light beams by the incident light coupler 322, and these two light beams respectively enter the incident light optical fibers 3231 and 3232, and then respectively irradiate on the test line 27 and the control line 28 of the test strip 15 in the test strip card 1 via the optical fiber probe 3241 for the test line of the test strip and the optical fiber probe 3242 for the control line of the test strip, to excite the reaction signifiers of the test line 27 and the control line 28 of the test strip to emit reflected light beams with the characteristic frequency, and the reflected light beams respectively pass through the optical fiber probe 3241 for the test line and the optical fiber probe 3242 for the control line, the corresponding emergent light optical fibers 3251, 3252 and the emergent light couplers 3261, 3262, and then enter the photoelectric detector 4 to be detected and converted into an electrical signal by the photoelectric detector 4; each of the optical fiber probes 3241, 3242 has a bundling and sharing structure, that is, an inner part of the optical fiber probe 3241 for the test line functions as the incident light optical fiber 3231, and an outer part of the optical fiber probe 3241 functions as the emergent light optical fiber 3251; while an inner part of the optical fiber probe 3242 for the control line functions as the incident light optical fiber 3232, and an outer part of the optical fiber probe 3242 functions as the emergent light optical fiber 3252.

A signal output terminal of the photoelectric detector 4 is connected with a signal input terminal of the analog-to-digital converter 5 via a signal amplifier. The photoelectric detector 4 may be selectively a CCD, a CMOS, a photoelectric multiplier tube, a photoelectric diode or a photoelectric triode.

The analog-to-digital converter 5, a signal output terminal of which is connected with a signal input terminal of the data processor 6, is configured to convert an amplified electrical signal transmitted by the photoelectric detector 4, which renders optical signals from the test line and the control line of the test strip, into a digital signal, and transmitting the digital signal to the data processor 6 for storing, processing and analyzing.

The data processor 6 is further connected with the electronic tag reading and writing module 10 with an antenna 11, the voice module 34, the cell box 7, the output display means 8, the plurality of keys 9 and the plurality of standby communication interfaces 31 on the surface of the testing device 2. The data processor 6 may be a microprocessor, a monolithic processor or a PC that has the corresponding data processing and controlling software. During the sample test, the data processor 6 automatically reads and/or writes the information of the electronic tag 20 in a non-contact mode via the electronic tag reading and writing module 10 with an antenna 11. The plurality of standby communication interfaces 31 on the surface of the testing device 2 are used by a detector to temporarily connect, according to detection requirements, a printer, a keyboard, a master computer or other external storage media with a USB serial port.

The output display means 8 may be an alphanumeric LCD screen, an LED, a touch display screen, a sound player or a master computer. The test strip testing system realizes the monocomponent and/or polycomponent quantitative or qualitative detection of a sample in conjunction with different output display means 8, that is, when the test strip testing system is used for the quantitative detection of a sample, the output display means 8 is an alphanumeric LCD screen, a touch display screen or a master computer; and when the test strip testing system is used for the qualitative detection of a sample, the output display means 8 is an LED or a sound player.

The voice module 34 is used for vocally outputting the sample test result information.

The cell box 7 is configured to receive a power supply which supplies power to the optical system 3, the photoelectric detector 4, the analog-to-digital converter 5 and the electronic tag reading and writing module 10 with an antenna 11 via the data processor 6.

When the test strip testing system is powered on for the sample test, the light emitted by the optical system 3 excites the reaction signifiers of the test line 27 and the control line 28 of the test strip to emit reflected light beams, and the reflected light beams are received by the photoelectric detector 4 and converted into electrical signals, which are then transmitted to the analog-to-digital converter 5 after being amplified and converted into digital signals to be transmitted to the data processor 6. The data processor 6 automatically identifies the optical signals with the characteristic frequency transmitted from the test line 27 and the control line 28, obtains the optical density value of the test line 27 ($OD_{test\ line}$) and the optical density value of the control line 28 ($OD_{control\ line}$) with respect to the detected substance, thereby calculating and obtaining a ratio of $OD_{test\ line}/OD_{control\ line}$ or a ratio of $OD_{test\ line}/(OD_{test\ line}+OD_{control\ line})$, and hence calculating the concentration of the detected substance and performing technical analysis according to the standard curve of the detected substance that is transmitting from the test strip card electronic tag 20 via the electronic tag reading and writing module 10, and then the testing result is transmitted to the output display means 8, and the voice module 34 vocally indicates the testing result information.

The data processor 6 of the test strip testing system may be further connected with a wireless communication module 12. The signal transmission end of the wireless communication module 12 may be in communication with the wireless network system 13, 14 that includes the remote server 14. The power supply in the cell box 7 further supplies power to the wireless communication module 12. The data processor 6 calculates and obtains a testing result according to the optical signals with the characteristic frequency transmitted from the test line 27 and the control line 28 in combination with a standard curve of the detected substance that is transmitted from the electronic tag 20 of the test strip card through the electronic tag reading and writing module 10; the testing result is transmitted to the output display means 8 for display, the voice module 34 vocally indicates the testing result information, and the testing result and the related information may be sent to the remote server 14 in the wireless network system 13, 14 via the wireless communication module 12 for data management and information consultation feedback.

The testing device 2 of the test strip testing system according to the invention is in general a portable instrument, a medium or large sized instrument, or a combination with a wireless communication product that has the corresponding information emitting and receiving functions, including a combination with one selected from a group consisted of: a mobile phone, a tablet computer, a personal digital assistant, a mobile terminal equipment and a computer.

The test strip 15 in the test strip card 1 of the test strip testing system according to the invention is disposable; the card box 16 of the test strip card 1 for receiving the test strip 15 and the electronic tag 20 installed on the card box 16 are matched with test strips of the same batch; and the testing device 2 is a durable general-purpose product.

The card box 16 of the test strip card 1 of the test strip testing system according to the invention is made of a thin rigid plastic material, a rigid paper material or other materials.

The method for preparing the test strip according to the invention includes the following steps of:

1) Preparing the Components of the Test Strip

I) the sample pad 21 is prepared as follows: a cellulose membrane is selected as the solid phase material for making the sample pad and cut into membrane blocks of a certain size, which are immerged in a sample pad treating liquid (i.e. pH=7.2 0.03 mol/L phosphate buffer+5% BSA+0.1% Tween 20), and then the membrane blocks are taken out and sufficiently dried;

II) the glass fiber membrane binding pad 22 is prepared as follows: a glass fiber membrane is selected as the solid phase material for making the binding pad and cut into membrane blocks of a certain size, a solution of a conjugate of the marker and the molecules related to the detection of the detected substance is added onto the membrane blocks, and then the membrane blocks are sufficiently dried;

III) the analysis membrane 23 is prepared as follows: a cellulose membrane is selected as the solid phase material of the analysis membrane and cut into membrane blocks of a certain size, another type of specific molecules related to the testing of the substance to be detected is applied on the membrane blocks at a distance interval from bottom to top starting from the bottom margin of the membrane to form test lines 27 and a quality control substance including secondary antibody is applied on the membrane blocks to form control lines 28, and then the membrane blocks are sufficiently dried;

IV) the super-absorbent pad 24 is prepared as follows: a cellulose membrane with a super-absorbent capability is cut into membrane blocks each of a certain size, which are then dried sufficiently;

V) the test strip reaction end position indication label 25 is prepared as follows: a fine pH indicator paper with a detectable pH value range from 5.0 to 9.0 is cut into membrane blocks each of a certain size, which are then dried sufficiently.

2) Assembling the Test Strip

The prepared components of the test strip, including the sample pad 21, the glass fiber membrane binding pad 22, the analysis membrane 23, the super-absorbent pad 24 and the test strip reaction end position indication label 25, are sequentially overlapped with one another and stuck on a plastic substrate 26, and the resultant product is cut into test strips of a certain size. The test strips are respectively packaged in test strip boxes and maintained in a dry condition.

The siphon and permeation reaction of the substance to be detected on the immunochromatographic test strip is a dynamic procedure. Due to the difference between the preparation processes and the raw materials for making different types of test strips or even same test strips of different batches, the sensitivity, stability and specificity of the test strips may be unnecessarily the same, thus the accuracy of the determined concentration of the detected substance may be influenced during the sample test. For example, due to the different sources of the cellulose membranes employed for manufacturing the test strips, the different membrane filtration pore sizes and different test strip thicknesses, reactants applied on the test strips may not travel at the same siphon and permeation speed, and some reactants may even reside along the permeation path before the test line 27 and the control line 28 of the test strip. Additionally, the samples might be tested by testers in different environment conditions, for example, the temperature difference and humidity difference between field on-site testing and indoor testing may influence the permeation speed of the test strip reactant on the test strip, thus the accurate determination of the concentration of the detected substance is influenced. In the invention, an electronic tag 20 is configured to store the corresponding standard curve for the detection of a substance using test strips of the same batch, or to store both the corresponding standard curve for the detection of a substance using test strips of the same batch and the reference optical density value ($OD_{control\ line}$) of the test strip, so that such problems may be well solved. The standard curve on the electronic tag 20 and the reference optical density value ($OD_{control\ line'}$) of the test strip control line has been calibrated considering the differences between test strips of different batches when the test strip card 1 is produced in the factory, to further improve the precision and flexibility of sample test. The standard curve for the detection of a substance, that is stored on the electronic tag 20, is used for sample test and quantification, and the stored reference optical density value ($OD_{control\ line'}$) of the test strip is used for indicating whether the reaction process of the test strip is successful, to determine whether the testing result is valid. During the practical detection of a sample, if the reaction of the test strip fails, a significant statistic error exists between the optical density $OD_{control\ line}$ of the control line obtained during the detection and the corresponding reference optical density value ($OD_{control\ line'}$) of the test strip that is read from the electronic tag 20.

A method for making the standard curve for the detected substance that is stored on the electronic tag 20 includes steps of: 1) preparing series concentrations of a standard product of the detected substance; 2) detecting the corresponding $OD_{test\ line}$ and $OD_{control\ line}$ for the series concentration of the standard product of the detected substance, thereby calculating the ratio of $OD_{test\ line}/OD_{control\ line}$ or the ratio of $OD_{test\ line}/(OD_{test\ line}+OD_{control\ line})$; 3) making a standard curve by taking the series concentration of the standard product as an X axis and taking the ratio of $OD_{test\ line}/OD_{control\ line}$ as a Y axis; or, drawing a standard curve by taking the series concentration of the standard product as the X axis and taking the ratio of $OD_{test\ line}/(OD_{test\ line}+OD_{control\ line})$ as the Y axis; and 4) establishing a standard curve software, and storing the curve software, the reference optical density value ($OD_{test\ line}$) of the test strip control line and the corresponding numerical value of the excited light characteristic wavelength and/or the numerical value of the reflected light characteristic wavelength used during detection on the electronic tag 20.

The sample test according to the invention is based on a positive correlation between the spectrum signal of the immunochromatographic test strip test line 27 and the concentration of the tested sample. The higher the concentration of the detected substance in the sample is, the stronger the reflected light signal with the characteristic frequency emitted by the reaction signifier that permeates to the test strip test line 27 will be. On the contrary, the lower the concentration of the detected substance in the sample is, the weaker the reflected light signal with the characteristic frequency emitted by the reaction signifier on the test strip test line 27 will be. According to such a relation, in the invention, the extended end of the test strip (i.e., the sample pad 21) inserted in the test strip card 1 is dipped into the sample, so that the liquid sample containing the detected substance slowly permeates to the back (proximal) end of the test strip under the capillary tube siphoning action of the microfiltration membrane of the test strip, as drawn by the super-absorbent pad 24 located on the other end of the test strip. If molecules of the detected substance (For example, antigen or antibody) exist in the liquid sample, the molecules are combined with the corresponding marked immune molecules coated on the glass fiber membrane binding pad 22 in the front and middle sections of the test strip, and permeate toward the back end of the test strip to the test line 27 of the analysis membrane 23 of the test strip, where they are combined with other specific related reaction molecules of the detected substance coated on the test line 27 (for example, another specific antibody or antigen of the molecules of the corresponding detected substance) to form a test line reaction signifier, and the remaining immuno-labeling molecules continue to permeate to the control line 28 of the test strip and are combined with the quality control substance (for example, a secondary antibody) pre-coated on the control line 28 to form a control line reaction signifier. The light emitted by the exciting light source 311, 321 of the optical system 3 passes through its output light path, automatically scans and excites the reaction signifiers of the test line 27 and the control line 28 of the test strip, so that an optical signal with the characteristic frequency is emitted; the optical signal with the characteristic frequency is received by the photoelectric detector 4 and converted into an electrical signal with the corresponding intensity; the electrical signal obtained from the conversion is amplified and then transmitted to the analog-to-digital converter 5, and converted by the analog-to-digital converter 5 into a digital signal, which is transmitted to the data processor 6 for storing and data processing. The data processor 6 automatically identifies the optical signals of the characteristic frequency from the test line 27 and the control line 28, obtains the optical density value of the test line 27 ($OD_{test\ line}$) and the optical density value of the control line 28 ($OD_{control\ line}$) of the detected substance, and calculates a ratio of $OD_{test\ line}/OD_{control\ line}$ or a ratio of $OD_{test\ line}/(OD_{test\ line}+OD_{control\ line})$; at the same time, the standard curve for the detected substance that is stored on the electronic tag 20 of the test strip card 1 is automatically read by the electronic tag reading and writing module 10 with an antenna 11, and the concentration of the detected substance is calculated in combination with the standard curve of the detected substance, then the output display means 8 displays the testing result, the voice module 34 vocally indicates the testing result information, and the testing result and the related information thereof are sent to the remote server 14 of the wireless network system 13 via the wireless communication module 12 for data management and information consultation feedback.

The sample according to the invention includes clinical or non-clinical blood, body fluid, urine, saliva, genital secretion, or other liquid samples or viscous samples, wherein, the clinical sample includes a sample of infectious disease, hormone, cardiovascular disease, tumour, cancer, diabetes and autoimmune disease, and the non-clinical sample includes a sample for food detection, environmental pollution detection, pesticide residue detection, biological contamination detection, biological agent detection, veterinary detection and drug detection. The invention carries out a monocomponent or polycomponent quantitative detection (including qualitative detection) on the object to be detected in the above samples.

A testing method of the test strip testing system according to the invention is realized by the following steps of:
1) powering on the test strip testing system;
2) inserting the test strip 15 into the test strip card 1, and then inserting the test strip card 1 inserted with the test strip into the test strip card receptacle 33 of the testing device 2 of the test strip testing system;
3) dipping the sample absorption end of the test strip into a sample;
4) pressing a detection key of the system to start the sample test by the test strip testing system, and after the sample test is completed, the output display means 8 displays the test strip testing result and the relevant information, and at the same time, the voice module 34 vocally indicates the testing result information; and
5) pressing the sending key to send the testing result and the information to the remote server 14 for data management and information consultation feedback.

BENEFICIAL EFFECTS OF THE INVENTION

In comparison with the prior art, the invention has the following beneficial effects:
1) The sample test is fast, and the quantitative testing result of a sample can be obtained rapidly and accurately in a few minutes; when the test strip for sample test is a quantum dot-marked test strip, the system of the invention can rapidly and accurately quantify index of a plurality of components in the sample simultaneously in a few minutes via a single operation. Quantum dot (QD), which was developed in 1990s, is a semiconductor nano crystal with good spectral features and photochemical stability, and has characteristics of a high fluorescence radiation efficiency, a wide range of excited spectrum, a narrow range of emission spectrum, a long fluorescence lifetime, a large Stokes displacement, a grain size approaching to a biologic molecule, and multifunctionalization after surface modification. As a new-generation biologic fluorescence marker, quantum dot has a profound and lasting potential to replace the traditional organic dyestuff. Quantum dots with different grain sizes, types and structures can generate a continuous luminescence spectrum peak at different characteristic wavelengths, further, the luminescence spectrum peaks at characteristic wavelengths generated by the quantum dot mixture do not overlap with one another. Therefore, if the corresponding reaction molecules of the detected substance are marked with different quantum dots respectively, and a mixture thereof is coated on a immunochromatographic test strip to react with a sample to be detected, the concentrations of a plurality of components of the sample can be detected rapidly and accurately in a few minutes by determining the specific fluorescence signal of the test strip.

2) The amount of the sample required for the sample testing is reduced, and several microliters to several dozens of microliters of the sample is sufficient for the testing.

3) The test strip testing system according to the invention may be embodied as a large-sized detection instrument for use by large, middle and small organizations, in this case, the data processor 6 of the test strip testing system may be embodied as a PC; or, the test strip testing system may be embodied as a small-sized portable detector for on-site instant detection in a family, a supermarket, a street, an invalid bed and in people's daily life, in this case, the data processor 6 may be embodied as a microprocessor.

4) The operation of the test strip testing system is simple and the quality control is convenient, so that an ordinary person can realize the rapid quantitative detection of multiple indexes of a sample without the aid of an additional equipment or reagent, thereby overcoming the limitation of the prior art where the sample test, especially quantitative detection of multiple components, must be operated by a professional technician. The function of the voice module 34 of the invention to output the testing result information vocally is helpful for operators with poor eyesight (for example, an elderly person) to listen to the testing result. To conduct the sample test in the invention, a detector only needs to insert on site a test strip 15 applied with a sample into a test strip card 1 on which an electronic tag corresponding to test strips of the same batch as the test strip 15 is installed, then insert the test strip card 1 inserted with the test strip into the test strip card receptacle 33 of the testing device 2 of the system, and then dip the sample absorption end of the extended test strip into the sample to be tested, after that, the testing result may be accurately obtained in a few minutes; moreover, by pressing a transmission key, the testing result information may be further sent on site to a remote server for data management and information consultation feedback. The detection is rapid, convenient and simple, and the result is objective with a high sensitivity.

5) The test strip 15 in the test strip card 1 is disposable; the card box 16 of the test strip card 1 for receiving the disposable test strip 15 and the electronic tag 20 installed on the card box 16 are matched with test strips of the same batch; and the test strip testing device 2 is a durable general-purpose product. To test a different sample, it only needs to place the corresponding test strip and the corresponding card box 16 of the test strip card 1 into the system, so that rapid quantitative detection of the sample may be realized. A testing device 2 may be donated to a loyal user, to attract the user to buy the disposable test strips 15 matching with the testing device 2 and the test strip card box 16 on which an electronic tag 20 matching with test strips of the same batch is installed. The test strip 15 and the card box 16 of the test strip card on which an electronic tag 20 is installed are inexpensive, and thus can be afforded by common consumers.

6) The detection quality is controlled by quadruple indexes synchronously, so that sample quantification will be more accurate: i) a control line 28 is provided on the test strip 15, and the optical density of the control line functions for a detection and comparison purpose; ii) a standard curve of the corresponding detected substance is stored in an electronic tag 20, and is used for accurately quantifying the concentration of the corresponding detected substance; iii) the reference optical density value ($OD_{control\ line'}$) of the control line of test strips of the same batch is stored in the electronic tag 20, for monitoring whether the reaction of the test strip is successful during sample test and indicating whether the testing result is valid; and iv) a test strip reaction end position indication label is provided on the test strip 15, for indicating whether the siphon and permeation chromatography of the test strip reactant on the test strip is sufficient, and whether the reaction reaches the end position.

7) The test strip testing system may be applied widely. The sample to be detected may be clinical or non-clinical blood (including whole blood, blood serum and blood plasma), body fluid, urine, saliva, genital secretion, or other liquid samples or viscous samples. The clinical sample includes a sample of infectious disease, hormone, cardiovascular disease, tumour, cancer, diabetes and autoimmune disease, etc.; and the non-clinical sample includes a sample for food detection, environmental pollution detection, pesticide residue detection, biological contamination detection, biological agent detection, veterinary detection, drug detection, etc.

8) Remote management and consultation feedback of the testing result information may be performed over the mobile Internet. A wireless communication module 12 may be built in the test strip testing system according to the invention, where the wireless communication module 12 is connected with the data processor 6, and the signal transmission end thereof is in communication with the wireless network system 13,14. The testing result and the related information thereof obtained by the data processor 6 may be transmitted via the wireless communication module 12 to a remote server 14 for the data management and information consultation feedback.

9) The chromatographic reaction process of the test strip may be monitored dynamically. In the invention, the concentration of the detected substance is automatically determined by the data processor 6 according to a ratio of $OD_{test\ line}/OD_{control\ line}$ or a ratio of $OD_{test\ line}/(OD_{test\ line}+OD_{control\ line})$ of the test line and the control line of the test strip in combination with the corresponding standard curve of the detected substance that is stored on an electronic tag 20. The electronic tag 20 further stores a reference optical density value ($OD_{control\ line'}$) of the control line with respect to a standard product of the detected substance, that is used for making the standard curve for the detection. If the detection reaction of the test strip fails, a significant statistic error exists between the optical density value $OD_{control\ line}$ of the control line obtained during the detection and the reference optical density value ($OD_{control\ line'}$) of the control line stored on the electronic tag 20, which indicates that the reaction of the test strip fails. Due to the difference between different batches of test strips, the standard curve on the electronic tag 20 and the reference optical density value ($OD_{control\ line'}$) of the control line are calibrated when the test strip card is produced in the factory, so that any difference in the detected concentration of the substance for detection, which is caused by the quality difference of different batches of test strips, may be overcome. The end of the test strip according to the invention is provided with a test strip reaction end position indication label 25 for indicating whether the test strip reactant has fully permeated to the locations of the test line 27 and the control line 28 of the test strip before the system starts sample test, so that the light emitted by the optical system 3 can be used for automatically scanning the test line 27 and the control line 28 of the test strip, thereby accurately obtaining the success or failure details of the reaction process. By dynamically monitoring the reaction process of the test strip, the validity and accuracy of the test strip reaction and the precision of the testing result may be guaranteed.

10) Individualization may be embodied by the sample test. A plurality of communication interfaces 31 are equipped on the surface of the testing device 2 of the test strip testing system according to the invention, including a printer interface, a keyboard interface, a master computer interface and other USB interfaces to which an external storage medium can be connected, wherein each interface may be connected with the data processor 6 via real-time plugging in/out, which is convenient for a detector to access and print the testing result information.

11) The testing device 2 of the test strip testing system is a durable general-purpose product, which may be used for a long term; the test strip 15 is a dry chemically sensitive membrane, which may be preserved for a long time at room temperature; the test strip card box 16, which is used for inserting a test strip during detection and on which an electronic tag 20 matched with test strips of the same batch is installed, is a continuous product that may be preserved for a long time.

| Reference Numbers | | | |
|---|---|---|---|
| 1: test strip card, | 2: testing device, | 3: optical system, | 4: photoelectric detector, |
| 5: analog-to-digital converter, | 6: data processor, | 7: cell box, | |
| 8: output display means, | 9: a plurality of keys, | | |
| 10: electronic tag reading and writing module, | | | |
| 11: antenna of electronic tag reading and writing module, | | | |
| 12: wireless communication module, | 13: wireless network system, | | |
| 14: remote server of wireless network system, | 15: test strip, | 16: test strip card box, | |
| 17: opening end of test strip card box, | | | |
| 18: notch on upper side of the opening end of the test strip card box, | | | |
| 19: insertion stop flag of test strip card box, | 20: electronic tag, | 21: sample pad, | |
| 22: binding pad, | 23: analysis membrane, | 24: super-absorbent pad, | |
| 25: test strip reaction end position indication label, | 26: substrate, | | |
| 27: test line, | 28: control line, | 29: verification window, | |
| 30: test strip reaction end position observation window, | | | |
| 31: a plurality of standby communication interfaces, | | | |
| 32: sample application hole, | 33: test strip card receptacle, | 34: voice module, | |
| 311: exciting light source, | 312: optical fiber bundle, | | |
| 313: collimating lens, | 314: dichroic mirror, | 315: front lens group, | |
| 316: filter plate, | 317: rear lens group, | 321: exciting light source, | |
| 322: incident light coupler, | 3231: incident light optical fiber, | | |
| 3241: optical fiber probe for test line of test strip, | 3251: emergent light optical fiber, | | |
| 3261: emergent light coupler, | 3232: incident light optical fiber, | | |
| 3242: optical fiber probe for control line of test strip, | | | |
| 3252: emergent light optical fiber, | 3262: emergent light coupler. | | |

DETAILED DESCRIPTION OF THE EMBODIMENTS

Embodiment 1

Structure, Work Flow and Testing Method of a Test Strip Testing System without Remote Data Management and Remote Information Feedback Capabilities According to the Invention (as Illustrated in Combination with FIGS. 1, 2, 5, 6, 7 and 8)

1. The Structure of the Test Strip Testing System

Figure 1:
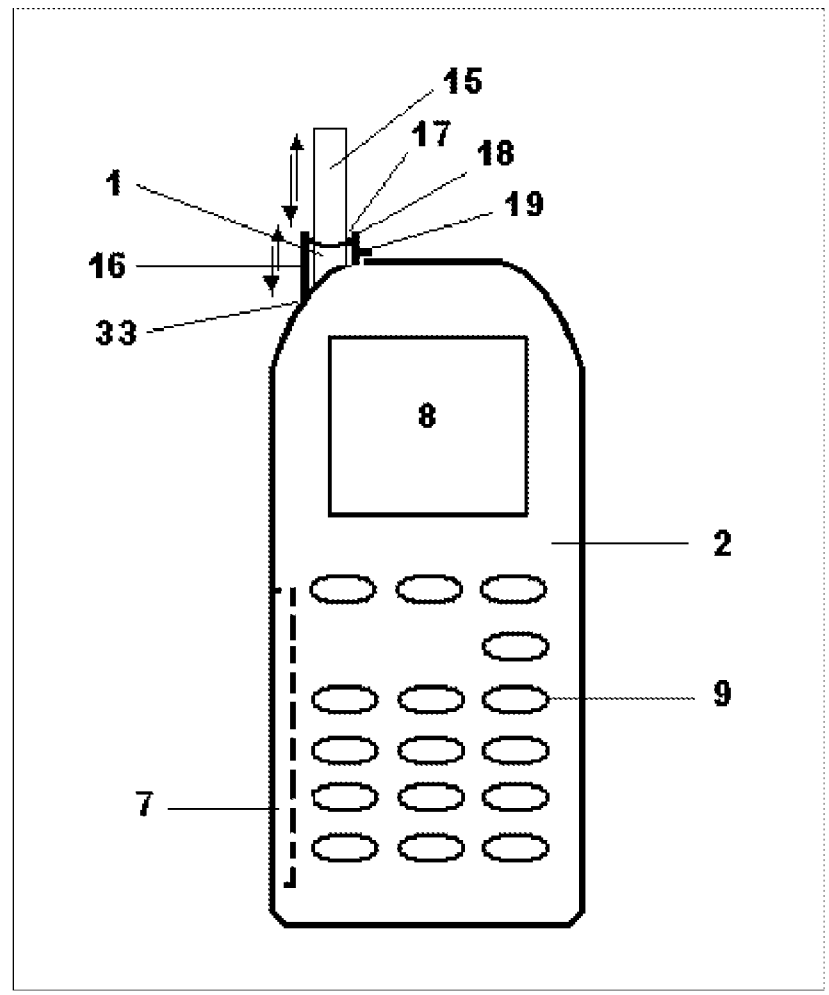
FIG. 1 is a block diagram showing an external structure of a test strip testing system including a testing device of a mobile phone form according to an embodiment of the invention, where the test strip testing system is without remote data management and remote information feedback capabilities.
Figure 2:
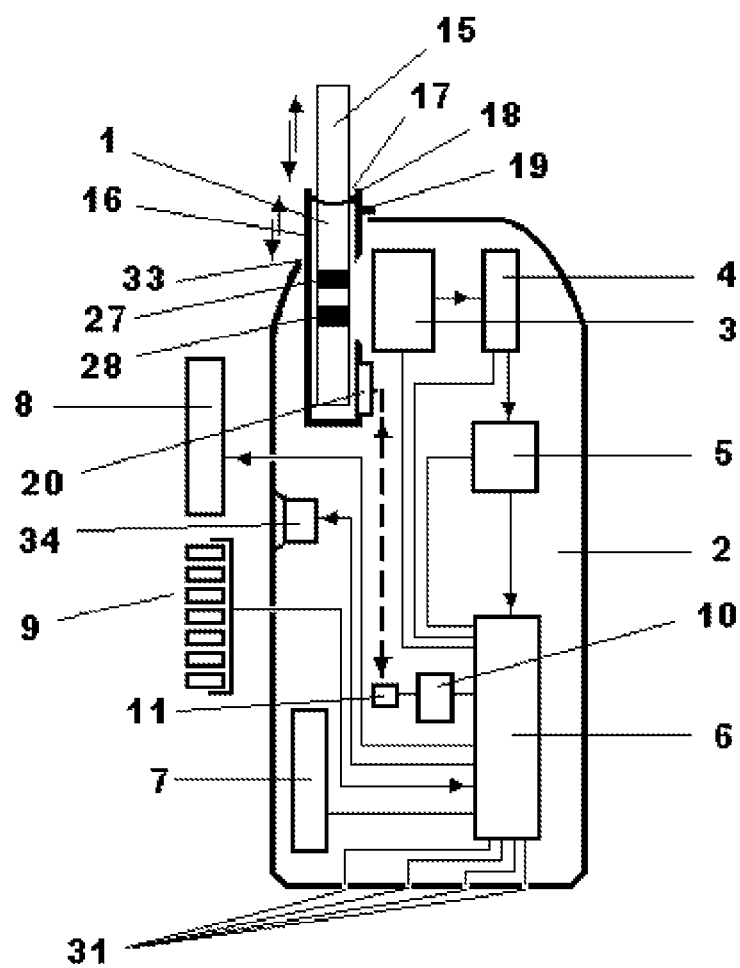
FIG. 2 is a block diagram showing an internal structure of the test strip testing system including the testing device of a mobile phone form according to the embodiment of the invention, where the test strip testing system is without remote data management and remote information feedback capabilities.

FIGS. 1 and 2 are block diagrams respectively showing the external and internal structures of a test strip testing system including a testing device of a mobile phone form according to an embodiment of the invention, where the test strip testing system is without remote data management and remote information feedback capabilities.

Referring to both FIGS. 1 and 2, the test strip testing system includes a test strip card 1 and a testing device 2. The test strip card 1 includes a card box 16, an optional test strip 15 inserted in the card box 16, and an electronic tag 20 that is installed on the card box 16 and configured to store test strip information. The testing device 2 includes an optical system 3, a photoelectric detector 4, an analog-to-digital converter 5, a data processor 6, an electronic tag reading and writing module 10 with an antenna 11, a voice module 34, a cell box 7, an output display means 8, a plurality of keys 9 located on the surface of the testing device 2, and a plurality of standby communication interfaces 31.

The test strip card 1 may be inserted into the testing device 2 as actually desired, and the test strip 15 may be inserted into the test strip card 1 as actually desired. The front end of the testing device 2 is provided with a test strip card receptacle 33. The test strip card 1, into which the test strip 15 has been inserted, may be inserted into the test strip card receptacle 33 for detecting a sample on the test strip.

The electronic tag 20 may be, but is not limited to, an RFD tag or a non-contact identification Integrated Circuit (IC) card, and installed anywhere in the test strip card box 16 in a film bonding, encapsulating and implanting, clamping, pinning or snapping manner. The electronic tag 20 stores a standard curve for the detection of a substance using test strips of the same batch for quantifying a sample concentration, or stores both a standard curve for the detection of a substance using test strips of the same batch for quantifying a sample concentration and a reference optical density value ($OD_{control\ line}$) of the test strip control line, and the electronic tag 20 stores the numerical value of a characteristic wavelength of the excited light and/or the numerical value of a characteristic wavelength of the reflected light, for the detection of the detected substance, and stores test strip information including a test strip batch number, test strip expiration date, electronic tag cryptogram, a reference value of a clinical index, test strip manufacturer information, etc., moreover, information such as identity information of the tested object, tester cryptogram, a sample name, a sample sequence number, test date and a test result is writable into the electronic tag 20. The electronic tag 20 may store various forms of standard curves, which include, but are not limited to, one from a group including: a correspondence curve between the series concentration of the standard product of the detected substance and $OD_{test\ line}/OD_{control\ line}$, and a correspondence curve between the series concentration of the standard product of the detected substance and $OD_{test\ line}/(OD_{test\ line}+OD_{control\ line})$. Herein, $OD_{test\ line}$ denotes the optical density value of the test line detected for the series concentration of the standard product of the detected substance, and $OD_{control\ line}$ denotes the optical density value of the control line detected for the series concentration of the standard product of the detected substance.

Figure 7:
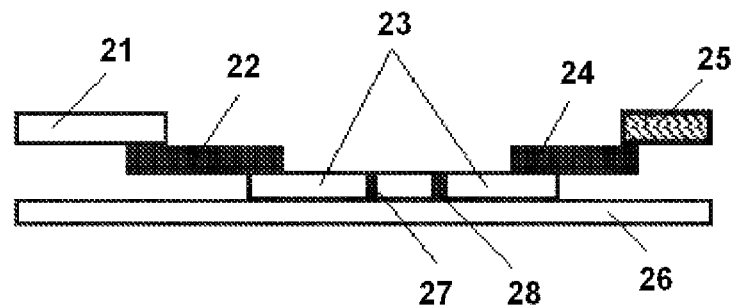
FIG. 7 is a side view of a test strip.
Figure 8:
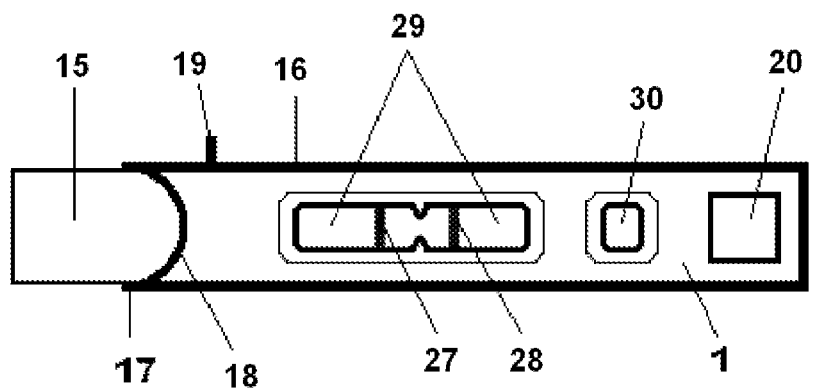
FIG. 8 is a top view of a test strip card.

The card box 16 of the test strip card 1 has an opening end 17 for inserting the test strip 15 as desired during the sample test. The upper side of the opening end 17 of the test strip card box is provided with a notch 18 for easily inserting the test strip 15 into the test strip card box 16. FIG. 7 is a side view of a test strip. FIG. 8 is a top view of a test strip card. As shown in FIGS. 7 and 8, the test strip 15 inserted into the test strip card 1 includes a sample pad 21, a glass fiber membrane binding pad 22 coated with a marker, an analysis membrane 23 with a test line 27 and a control line 28, a super-absorbent pad 24 and a test strip reaction end position indication label 25, which are arranged sequentially and stuck mutually. The sample absorption end (i.e., the sample pad 21) of the test strip 15 inserted into the card box 16 extends out of the opening end 17 of the test strip card box, to allow the test strip 15 to dip into and absorb a sample. The upper side of the test strip card box 16 has a verification window 29 at a location corresponding to the test line and the control line of the test strip in the card box, and a test strip reaction end position observation window 30 is provided at a location corresponding to the reaction end position indication label 25 of the test strip in the card box. A test strip card insertion stop flag 19 is arranged on the surface of the test strip card 1 at a location corresponding to the test strip card receptacle 33 of the testing device 2. The test strip 15 inserted into the test strip card 1 may be any test strip, which includes, but is not limited to, a quantum dot-marked test strip, a colloidal gold-marked test strip, a colloidal selenium-marked test strip, an upconversion phosphorescence-marked test strip, a nano rare earth fluorescent complex-marked test strip, a temporal resolution chromatography test strip, a chemiluminescence test strip, and so on.

An imaging signal terminal of the optical system 3 is connected with the photoelectric detector 4. The optical system 3 may be implemented in various schemes, which include, but are not limited to, the scheme shown in FIG. 5 and the scheme shown in FIG. 6.

Figure 5:
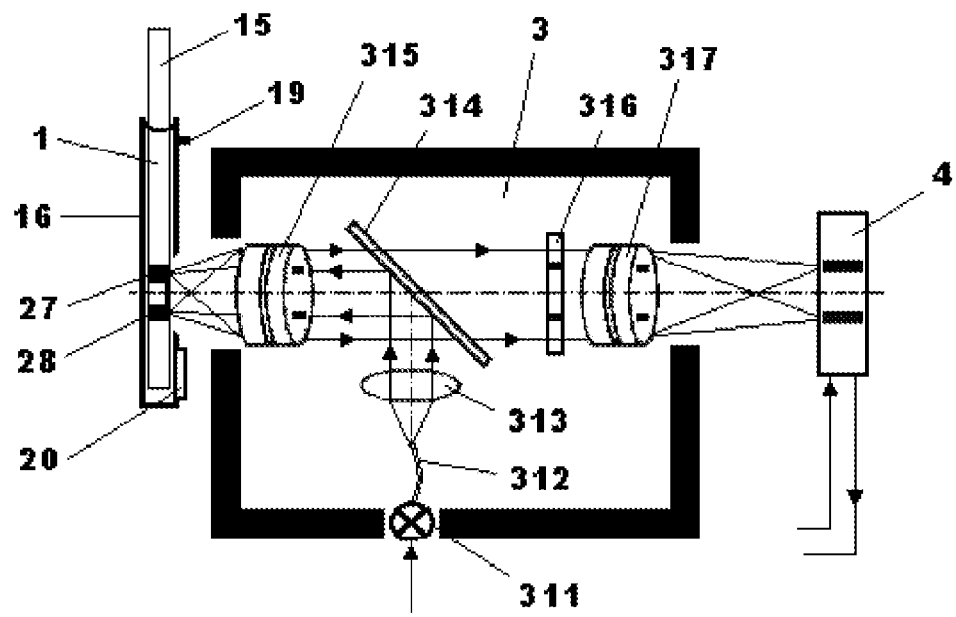
FIG. 5 is a block diagram showing the structure of a first optical system scheme of the test strip testing system according to an embodiment of the invention.

In the scheme of FIG. 5, the optical system 3 includes an illuminating system and an imaging system. The illuminating system includes an exciting light source 311. An optical fiber bundle 312, a collimating lens 313, a dichroic mirror 314, and a front lens group 315 form the output light path from the light source 311 to the test strip card 1. The exciting light source 311 includes a light-emitting diode LED or a laser diode. The imaging system includes a front lens group 315, a dichroic mirror 314, a filter plate 316 and a rear lens group 317 that are arranged coaxially. An included angle of 45° is formed between the reflecting surface of the dichroic mirror 314 and the optical axis. The front lens group 315 and the rear lens group 317 both employ an isolated structure. The light path of the illuminating system before the dichroic mirror 314 is vertical to the optical axis of the imaging system, and the light path of the illuminating system after the dichroic mirror 314 is arranged coaxially with the imaging system. The photoelectric detector 4 is located on an image plane of the rear lens group 317. The optical fiber bundle 312 divides the light emitted by the light source 311 into two laser beams with the same intensity that are spaced apart from each other, and these two laser beams are collimated by the collimating lens 313 into two parallel light beams that irradiate on the surface of the dichroic mirror 314, and synchronously irradiate on the test line 27 and the control line 28 of the test strip 15 in the test strip card 1 that are located in the object plane of the front lens group 315 via the front lens group 315 after being reflected by the dichroic mirror 314, to excite the test strip reaction signifier that permeates to the test line 27 and the control line 28 to emit reflected light with a characteristic frequency. The reflected light from the test line 27 and the control line 28 passes through the same front lens group 315 and the dichroic mirror 314, is filtered by the filter plate 316 to filter out parasitic light, exits from the rear lens group 317, and then enters into the photoelectric detector 4 to be detected and converted into an electrical signal by the photoelectric detector 4.

Figure 6:
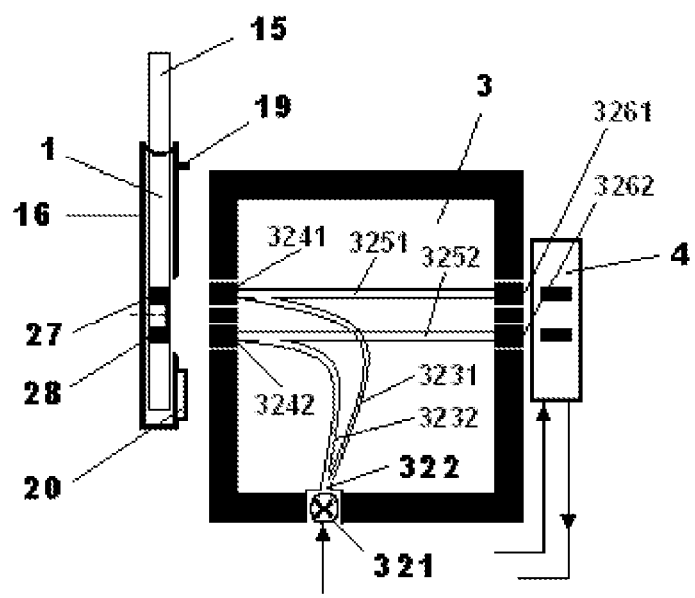
FIG. 6 is a block diagram showing the structure of a second optical system scheme of the test strip testing system according to an embodiment of the invention.

In the solution of FIG. 6, the optical system 3 includes an exciting light source 321, and an incident light coupler 322, incident light optical fibers 3231 and 3232, optical fiber probes 3241 and 3242, emergent light optical fibers 3251 and 3252, and emergent light couplers 3261 and 3262 form the output light path from the exciting light source 321 to the photoelectric detector 4. The exciting light source 321 includes a light-emitting diode LED or a laser diode. The light emitted by the light source 321 is divided into two light beams by the incident light coupler 322, and these two light beams respectively enter the incident light optical fibers 3231 and 3232, and then respectively irradiate on the test line 27 and the control line 28 of the test strip 15 in the test strip card 1 via the optical fiber probe 3241 for the test strip test line and the optical fiber probe 3242 for the test strip control line, so as to excite the reaction signifiers of the test line 27 and the control line 28 of the test strip to emit reflected light beams with the characteristic frequency. The two reflected light beams from the test line 27 and the control line 28 respectively pass through the optical fiber probe 3241 for the test line and the optical fiber probe 3242 for the control line, the corresponding emergent light optical fibers 3251 and 3252, and the emergent light couplers 3261 and 3262, and then enter the photoelectric detector 4 to be detected and converted into electrical signals by the photoelectric detector 4. Each of the optical fiber probes 3241 and 3242 employs a bundling and sharing structure, that is, the inner part of the optical fiber probe 3241 for the test line functions as the incident light optical fiber 3231, and the outer part thereof functions as the emergent light optical fiber 3251; likewise, the inner part of the optical fiber probe 3242 for the control line functions as the incident light optical fiber 3232, and the outer part thereof functions as the emergent light optical fiber 3252.

A signal output terminal of the photoelectric detector 4 is connected with a signal input terminal of the analog-to-digital converter 5 via a signal amplifier. The photoelectric detector 4 may be any one from a group including CCD, CMOS, photoelectric multiplier tube, photoelectric diode and photoelectric triode.

A signal output terminal of the analog-to-digital converter 5 is connected with a signal input terminal of the data processor 6, so that the amplified electrical signal transmitted from the photoelectric detector 4 to the analog-to-digital converter 5, which represents the optical signal from the test line and the optical signal from the control line of the test strip, is converted into a digital signal, which is then transmitted to the data processor 6 to be stored, processed and analyzed.

The data processor 6 is further connected with the electronic tag reading and writing module 10 provided with an antenna 11, the voice module 34, the cell box 7, the output display means 8, the plurality of keys 9 on the surface of the testing device 2, and the plurality of standby communication interfaces 31. The data processor 6 is a microprocessor, a monolithic processor or a personal computer (PC) that has the corresponding data processing and controlling software. During a sample test, the data processor 6 automatically reads and/or writes the information on the electronic tag 20 in a non-contact mode via the electronic tag reading and writing module 10 with an antenna 11. The plurality of standby communication interfaces 31 on the surface of the testing device 2 are configured to temporarily connect with a printer, a keyboard, a master computer or other external storage media with a USB serial port, depending on test needs.

The output display means 8 may be an alphanumeric LCD screen, an LED, a touch display screen, a sound player, a master computer, etc. The test strip testing system realizes the quantitative or qualitative detection of one or more components in a sample in conjunction with different output display means 8. Particularly, when the test strip testing system is used for the quantitative detection of a sample, the output display means 8 may be an alphanumeric LCD screen, a touch display screen or a master computer; and when the test strip testing system is used for the qualitative detection of a sample, the output display means 8 may be an LED or a sound player.

The voice module 34 is used for vocally outputting information of the sample test result.

A power supply in the cell box 7 is configured to supply power to the optical system 3, the photoelectric detector 4, the analog-to-digital converter 5, the electronic tag reading and writing module 10 with an antenna 11 via the data processor 6.

The test strip testing device 2 is generally a portable instrument, a medium or large sized instrument, or a combination with a wireless communication product that has the corresponding information transmitting and receiving functions, including a combination with one selected from a group consisted of: a mobile phone, a tablet computer, a personal digital assistant, a mobile terminal equipment and a computer.

The test strip 15 in the test strip card 1 is a disposable test strip, but the card box 16 of the test strip card 1 for receiving the test strip 15 and the electronic tag 20 attached to the card box 16 match with test strips of the same batch, and the testing device 2 is a durable general-purpose product.

The card box 16 of the test strip card 1 is made of thin rigid plastic, rigid paper or other materials.

2. The Operating Principle and Working Process of the Test Strip Testing System

During a sample test, the test strip 15 is inserted into the test strip card 1, then the test strip card 1 containing the test strip is inserted into the test strip card receptacle 33 of the testing device 2, and a sample absorption end 21 (i.e. the distal end) of the test strip extending from the test strip card 1 is dipped into a liquid sample. As drawn by the superabsorbent pad 24 located on the opposite end of the test strip, the liquid sample of the detected substance at the sample absorption end 21 of the test strip slowly permeates to the back end (i.e. the proximal end) of the test strip under the capillary tube siphoning action of the microfiltration membrane. If molecules of the target substance be tested (for example, antigen or antibody) exist in the liquid sample, the molecules will be combined with the corresponding marked immune molecules coated on the glass fiber membrane binding pad 22 in the distal and middle sections of the test strip, and permeate toward the proximal end of the test strip to the test line 27 of the analysis membrane 23 of the test strip, where the molecules are combined with another type of specific reaction molecules (for example, another specific antibody or antigen of the corresponding molecules of the detected substance) coated on the test line 27 to form a test line reaction signifier, and a part of the remaining immunolabeling molecules continue to permeate to the control line 28 of the test strip and are combined with the quality control substance (for example, a secondary antibody) pre-coated on the control line 28 to form a control line reaction signifier. After being excited by the light emitted by the optical system 3, the reaction signifiers of the test line 27 and the control line 28 of the test strip emits reflected light with the characteristic frequency, and the reflected light signal from the test strip test line 27 has a positive correlation with the concentration of the sample to be tested. The higher the concentration of the detected substance in the sample is, the stronger the optical signal with the characteristic frequency emitted from the test strip test line 27 will be. On the contrary, the lower the concentration of the detected substance in the sample is, the weaker the optical signal with the characteristic frequency emitted from the test strip test line 27 will be. Thereby, the concentration of the detected substance in the sample may be quantified. As such, the light emitted by the optical system 3 excites the reaction signifiers of the test line 27 and the control line 28 of the test strip to emit reflected light with the characteristic frequency, which is received and converted into an electrical signal by the photoelectric detector 4; and the resultant electrical signal, after being amplified, is transmitted to and converted into a digital signal by the analog-to-digital converter 5 and then transmitted to the data processor 6 for storing and data processing. The data processor 6 automatically identifies the optical signals with the characteristic frequency transmitted from the test line 27 and the control line 28, and obtains the optical density value of the test line 27 ($OD_{test\ line}$) and the optical density value of the control line 28 ($OD_{control\ line}$) of the detected substance, from which the ratio of $OD_{test\ line}/OD_{control\ line}$ or the ratio of $OD_{test\ line}/(OD_{test\ line}+OD_{control\ line})$ is calculated; at the same time, the standard curve for the detected substance stored on the electronic tag 20 of the test strip card 1 is automatically read by the electronic tag reading and writing module 10 with an antenna 11, the concentration of the detected substance is calculated in combination with the standard curve for the detected substance, and the testing result is transmitted to the output display means 8, where the voice module 34 vocally indicates the testing result information.

3. The Making and Storing of the Standard Curve for the Test Substance

Various standard curves for the test substance may be stored on the electronic tag, and the standard curves include, but are not limited to, one of a correspondence curve between the series concentration of the standard product of the detected substance and $OD_{test\ line}/OD_{control\ line}$ and a correspondence curve between the series concentration of the standard product of the detected substance and $OD_{test\ line}/(OD_{test\ line}+OD_{control\ line})$. Herein, $OD_{test\ line}$ denotes the optical density value of the test line detected for the series concentration of the standard product of the detected substance, and $OD_{control\ line}$ denotes the optical density value of the control line detected for the series concentration of the standard product of the detected substance.

The method for making the standard curve includes:

1) preparing the series concentration of a standard product of the detected substance;

2) detecting the corresponding $OD_{test\ line}$ and $OD_{control\ line}$ for the series concentration of the standard product of the detected substance, thereby calculating the ratio of $OD_{test\ line}/OD_{control\ line}$ or the ratio of $OD_{test\ line}/(OD_{test\ line}+OD_{control\ line})$;

3) making a standard curve by taking the series concentration of the standard product as an X axis and taking the ratio of $OD_{test\ line}/OD_{control\ line}$ as a Y axis; or, drawing a standard curve by taking the series concentration of the standard product as the X axis and taking the ratio of $OD_{test\ line}/(OD_{test\ line}+OD_{control\ line})$ as the Y axis;

4) establishing a standard curve software, and storing the established software on the electronic tag 20; and 5) storing the optical density value ($OD_{control\ line}$) for the test strip control line obtained when making the standard curve and the corresponding numerical value of the characteristic wavelength of the excited light and/or the numerical value of the characteristic wavelength of the reflected light that are used during detection, together with the standard curve, on the electronic tag 20; during the practical detection of a sample, the optical density value ($OD_{control\ line}$) for the test strip control line stored on the electronic tag 20 functions to monitor the success or failure of the test strip reaction (here, the reference optical density value for the test strip control line is represented by $OD_{control\ line'}$), and if the test strip reaction fails, a great statistic error may exist between the $OD_{control\ line}$ obtained during the sample test and the corresponding reference optical density value $OD_{control\ line'}$ stored on the electronic tag 20; here, the parameters stored on the electronic tag are matched with the test strip products of the same batch.

4. Testing Method for the Test Strip Testing System

A testing method for the test strip testing system is realized by the following steps of:

1) powering on the test strip testing system;

2) inserting the test strip 15 into the test strip card 1, and then inserting the test strip card 1 inserted with the test strip into the test strip card receptacle 33 of the testing device 2 of the test strip testing system;

3) dipping the sample absorption end of the test strip into a sample; and 4) pressing a detection key of the system to start the sample test by the test strip testing system, and after the sample test is completed, the output display means 8 displays the test strip testing result and the relevant information, and at the same time, the voice module 34 vocally indicates the testing result information.

Embodiment 2

Structure, Work Flow and Testing Method of a Test Strip Testing System with Remote Data Management and Remote Information Consultation Feedback Capabilities According to the Invention (as Illustrated in Combination with FIGS. 3, 4, 5, 6, 7 and 8)

1. The Structure of the Test Strip Testing System

Figure 3:
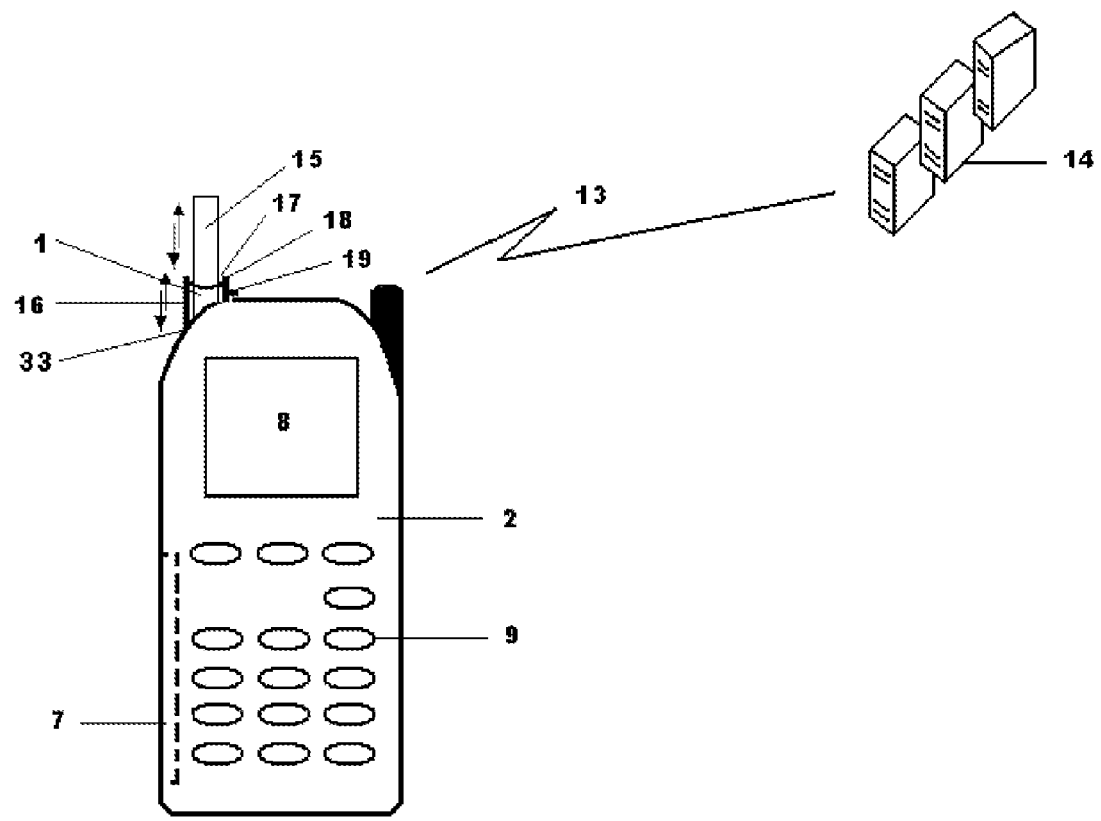
FIG. 3 is a block diagram showing an external structure of a test strip testing system including a testing device of a mobile phone form according to an embodiment of the invention, where the test strip testing system has remote data management and remote information consultation feedback capabilities.
Figure 4:
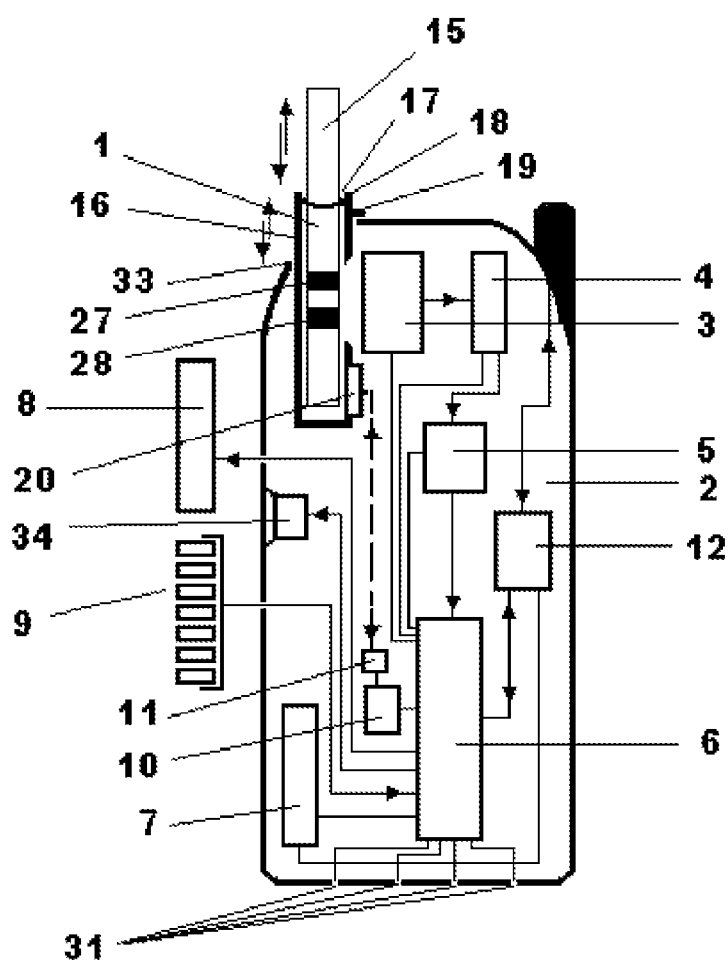
FIG. 4 is a block diagram showing an internal structure of the test strip testing system including the testing device of a mobile phone form according to the embodiment of the invention, where the test strip testing system has remote data management and remote information consultation feedback capabilities.

FIGS. 3 and 4 are block diagrams respectively showing the external and internal structures of a test strip testing system including a testing device of a mobile phone form according to an embodiment of the invention, where the test strip testing system has remote data management and remote information consultation feedback capabilities.

Referring to both FIGS. 3 and 4, the test strip testing system includes a test strip card 1, a testing device 2 and a wireless network system 13 that includes a remote server 14. The test strip card 1 includes a card box 16, an optional test strip 15 inserted in the card box 16, and an electronic tag 20 that is installed on the card box 16 and configured to store test strip information. The testing device 2 includes an optical system 3, a photoelectric detector 4, an analog-to-digital converter 5, a data processor 6, an electronic tag reading and writing module 10 with an antenna 11, a voice module 34, a cell box 7, an output display means 8, a plurality of keys 9 located on the surface of the testing device 2, and a plurality of standby communication interfaces 31.

The test strip card 1 may be inserted into the testing device 2 as actually desired, and the test strip 15 may be inserted into the test strip card 1 as actually desired. The front end of the testing device 2 is provided with a test strip card receptacle 33. The test strip card 1, into which the test strip 15 has been inserted, may be inserted into the test strip card receptacle 33 for detecting a sample on the test strip.

The electronic tag 20 may be, but is not limited to, an RFID tag or a non-contact identification Integrated Circuit (IC) card, and installed anywhere in the test strip card box 16 in a film bonding, encapsulating and implanting, clamping, pinning or snapping manner. The electronic tag 20 stores a standard curve for the detection of a substance using test strips of the same batch for quantifying a sample concentration, or stores both a standard curve for the detection of a substance using test strips of the same batch for quantifying a sample concentration and a reference optical density value ($OD_{control\ line}$) of the test strip control line, and the electronic tag 20 stores the numerical value of a characteristic wavelength of the excited light and/or the numerical value of a characteristic wavelength of the reflected light, for the detection of the detected substance, and stores test strip information including a test strip batch number, test strip expiration date, electronic tag cryptogram, a reference value of a clinical index, test strip manufacturer information, etc., moreover, information such as identity information of the tested object, tester cryptogram, a sample name, a sample sequence number, test date and a test result is writable into the electronic tag 20. The electronic tag 20 may store various forms of standard curves, which include, but are not limited to, one from a group including: a correspondence curve between the series concentration of the standard product of the detected substance and $OD_{test\ line}/OD_{control\ line}$, and a correspondence curve between the series concentration of the standard product of the detected substance and $OD_{test\ line}/(OD_{test\ line}+OD_{control\ line})$. Herein, $OD_{test\ line}$ denotes the optical density value of the test line detected for the series concentration of the standard product of the detected substance, and $OD_{control\ line}$ denotes the optical density value of the control line detected for the series concentration of the standard product of the detected substance.

The card box 16 of the test strip card 1 has an opening end 17 for inserting the test strip 15 as desired during the sample test. The upper side of the opening end 17 of the test strip card box is provided with a notch 18 for easily inserting the test strip 15 into the test strip card box 16. FIG. 7 is a side view of a test strip. FIG. 8 is a top view of a test strip card. As shown in FIGS. 7 and 8, the test strip 15 inserted into the test strip card 1 includes a sample pad 21, a glass fiber membrane binding pad 22 coated with a marker, an analysis membrane 23 with a test line 27 and a control line 28, a super-absorbent pad 24 and a test strip reaction end position indication label 25, which are arranged sequentially and stuck mutually. The sample absorption end (i.e., the sample pad 21) of the test strip 15 inserted into the card box 16 extends out of the opening end 17 of the test strip card box, to allow the test strip 15 to dip into and absorb a sample. The upper side of the test strip card box 16 has a verification window 29 at a location corresponding to the test line and the control line of the test strip in the card box, and a test strip reaction end position observation window 30 is provided at a location corresponding to the reaction end position indication label 25 of the test strip in the card box. A test strip card insertion stop flag 19 is arranged on the surface of the test strip card 1 at a location corresponding to the test strip card receptacle 33 of the testing device 2. The test strip 15 inserted into the test strip card 1 may be any test strip, which includes, but is not limited to, a quantum dot-marked test strip, a colloidal gold-marked test strip, a colloidal selenium-marked test strip, an upconversion phosphorescence-marked test strip, a nano rare earth fluorescent complex-marked test strip, a temporal resolution chromatography test strip, a chemiluminescence test strip, and so on.

An imaging signal terminal of the optical system 3 is connected with the photoelectric detector 4. The optical system 3 may be implemented in various schemes, which include, but are not limited to, the scheme shown in FIG. 5 and the scheme shown in FIG. 6.

In the scheme of FIG. 5, the optical system 3 includes an illuminating system and an imaging system. The illuminating system includes an exciting light source 311. An optical fiber bundle 312, a collimating lens 313, a dichroic mirror 314, and a front lens group 315 form the output light path from the light source 311 to the test strip card 1. The exciting light source 311 includes a light-emitting diode LED or a laser diode. The imaging system includes a front lens group 315, a dichroic mirror 314, a filter plate 316 and a rear lens group 317 that are arranged coaxially. An included angle 45° is formed between the reflecting surface of the dichroic mirror 314 and the optical axis. The front lens group 315 and the rear lens group 317 both employ an isolated structure. The light path of the illuminating system before the dichroic mirror 314 is vertical to the optical axis of the imaging system, and the light path of the illuminating system after the dichroic mirror 314 is arranged coaxially with the imaging system. The photoelectric detector 4 is located on an image plane of the rear lens group 317. The optical fiber bundle 312 divides the light emitted by the light source 311 into two laser beams with the same intensity that are spaced apart from each other, and these two laser beams are collimated by the collimating lens 313 into two parallel light beams that irradiate on the surface of the dichroic mirror 314, and synchronously irradiate on the test line 27 and the control line 28 of the test strip 15 in the test strip card 1 that are located in the object plane of the front lens group 315 via the front lens group 315 after being reflected by the dichroic mirror 314, to excite the test strip reaction signifier that permeates to the test line 27 and the control line 28 to emit reflected light with a characteristic frequency. The reflected light from the test line 27 and the control line 28 passes through the same front lens group 315 and the dichroic mirror 314, is filtered by the filter plate 316 to filter out parasitic light, exits from the rear lens group 317, and then enters into and then detected and converted by the photoelectric detector 4 into an electrical signal.

In the solution of FIG. 6, the optical system 3 includes an exciting light source 321, and an incident light coupler 322, incident light optical fibers 3231 and 3232, optical fiber probes 3241 and 3242, emergent light optical fibers 3251 and 3252, and emergent light couplers 3261 and 3262 form the output light path from the exciting light source 321 to the photoelectric detector 4. The exciting light source 321 includes a light-emitting diode LED or a laser diode. The light emitted by the light source 321 is divided into two light beams by the incident light coupler 322, and these two light beams respectively enter the incident light optical fibers 3231 and 3232, and then respectively irradiate on the test line 27 and the control line 28 of the test strip 15 in the test strip card 1 via the optical fiber probe 3241 for the test strip test line and the optical fiber probe 3242 for the test strip control line, so as to excite the reaction signifier of the test line 27 and the control line 28 of the test strip to emit reflected light beams with the characteristic frequency. The two reflected light beams from the test line 27 and the control line 28 respectively pass through the optical fiber probe 3241 for the test line and the optical fiber probe 3242 for the control line, the corresponding emergent light optical fibers 3251 and 3252, and the emergent light couplers 3261 and 3262, and then enter the photoelectric detector 4 to be detected and converted into electrical signals by the photoelectric detector 4. Each of the optical fiber probes 3241 and 3242 employs a bundling and sharing structure, that is, the inner part of the optical fiber probe 3241 for the test line functions as the incident light optical fiber 3231, and the outer part thereof functions as the emergent light optical fiber 3251; likewise, the inner part of the optical fiber probe 3242 for the control line functions as the incident light optical fiber 3232, and the outer part thereof functions as the emergent light optical fiber 3252.

A signal output terminal of the photoelectric detector 4 is connected with a signal input terminal of the analog-to-digital converter 5 via a signal amplifier. The photoelectric detector 4 may be any one from a group including CCD, CMOS, photoelectric multiplier tube, photoelectric diode and photoelectric triode.

A signal output terminal of the analog-to-digital converter 5 is connected with a signal input terminal of the data processor 6, so that the amplified electrical signal transmitted from the photoelectric detector 4 to the analog-to-digital converter 5, which represents the optical signal from the test line and the optical signal from the control line of the test strip, is converted into a digital signal, which is then transmitted to the data processor 6 to be stored, processed and analyzed.

The data processor 6 is further connected with the electronic tag reading and writing module 10 provided with an antenna 11, a wireless communication module 12, the voice module 34, the cell box 7, the output display means 8, the plurality of keys 9 on the surface of the testing device 2, and the plurality of standby communication interfaces 31. The data processor 6 is a microprocessor, a monolithic processor or a personal computer (PC) that has the corresponding data processing and controlling software. During a sample test, the data processor 6 automatically reads and/or writes the information on the electronic tag 20 in a non-contact mode via the electronic tag reading and writing module 10 with an antenna 11. The plurality of standby communication interfaces 31 on the surface of the testing device 2 are configured to temporarily connect with a printer, a keyboard, a master computer or other external storage media with a USB serial port, depending on test needs.

The signal transmission end of the wireless communication module 12 is configured to communicate with the wireless network system 13, 14 that includes the remote server 14.

The output display means 8 may be an alphanumeric LCD screen, an LED, a touch display screen, a sound player, a master computer, etc. The test strip testing system realizes the quantitative or qualitative detection of one or more components in a sample in conjunction with different output display means 8. Particularly, when the test strip testing system is used for the quantitative detection of a sample, the output display means 8 may be an alphanumeric LCD screen, a touch display screen or a master computer; and when the test strip testing system is used for the qualitative detection of a sample, the output display means 8 may be an LED or a sound player.

The voice module 34 is used for vocally outputting information of the sample test result.

A power supply in the cell box 7 is configured to supply power to the optical system 3, the photoelectric detector 4, the analog-to-digital converter 5, the electronic tag reading and writing module 10 with an antenna 11 via the data processor 6. The power supply in the cell box 7 is further configured to supply power to the wireless communication module 12.

The test strip testing device 2 is generally a portable instrument, a medium or large sized instrument, or a combination with a wireless communication product that has the corresponding information transmitting and receiving functions, including a combination with one selected from a group consisted of: a mobile phone, a tablet computer, a personal digital assistant, a mobile terminal equipment and a computer.

The test strip 15 in the test strip card 1 is a disposable test strip, but the card box 16 of the test strip card 1 for receiving the test strip 15 and the electronic tag 20 attached to the card box 16 match with test strips of the same batch, and the testing device 2 is a durable general-purpose product.

The card box 16 of the test strip card 1 is made of thin rigid plastic, rigid paper or other materials.

2. The Operating Principle and Working Process of the Test Strip Testing System

During a sample test, the test strip 15 is inserted into the test strip card 1, then the test strip card 1 containing the test strip is inserted into the test strip card receptacle 33 of the testing device 2, and a sample absorption end 21 (i.e. the distal end) of the test strip extending from the test strip card 1 is dipped into a liquid sample. As drawn by the superabsorbent pad 24 located on the opposite end of the test strip, the liquid sample of the detected substance at the sample absorption end 21 of the test strip slowly permeates to the back end (i.e. the proximal end) of the test strip under the capillary tube siphoning action of the microfiltration membrane. If molecules of the target substance be tested (for example, antigen or antibody) exist in the liquid sample, the molecules will be combined with the corresponding marked immune molecules coated on the glass fiber membrane binding pad 22 in the distal and middle sections of the test strip, and permeate toward the proximal end of the test strip to the test line 27 of the analysis membrane 23 of the test strip, where the molecules are combined with another type of specific reaction molecules (for example, another specific antibody or antigen of the corresponding molecules of the detected substance) coated on the test line 27 to form a test line reaction signifier, and a part of the remaining immunolabeling molecules continue to permeate to the control line 28 of the test strip and are combined with the quality control substance (for example, a secondary antibody) pre-coated on the control line 28 to form a control line reaction signifier. After being excited by the light emitted by the optical system 3, the reaction signifiers of the test line 27 and the control line 28 of the test strip emits reflected light with the characteristic frequency, and the reflected light signal from the test strip test line 27 has a positive correlation with the concentration of the sample to be tested. The higher the concentration of the detected substance in the sample is, the stronger the optical signal with the characteristic frequency emitted from the test strip test line 27 will be. On the contrary, the lower the concentration of the detected substance in the sample is, the weaker the optical signal with the characteristic frequency emitted from the test strip test line 27 will be. Thereby, the concentration of the detected substance in the sample may be quantified. As such, the light emitted by the optical system 3 excites the reaction signifiers of the test line 27 and the control line 28 of the test strip to emit reflected light with the characteristic frequency, which is received and converted into an electrical signal by the photoelectric detector 4; and the resultant electrical signal, after being amplified, is transmitted to and converted into a digital signal by the analog-to-digital converter 5 and then transmitted to the data processor 6 for storing and data processing. The data processor 6 automatically identifies the optical signals with the characteristic frequency transmitted from the test line 27 and the control line 28, and obtains the optical density value of the test line 27 ($OD_{test\ line}$) and the optical density value of the control line 28 ($OD_{control\ line}$) of the detected substance, from which the ratio of $OD_{test\ line}/OD_{control\ line}$ or the ratio of $OD_{test\ line}/(OD_{test\ line}+OD_{control\ line})$ is calculated; at the same time, the standard curve for the detected substance stored on the electronic tag 20 of the test strip card 1 is automatically read by the electronic tag reading and writing module 10 with an antenna 11, the concentration of the detected substance is calculated in combination with the standard curve for the detected substance, and the testing result is transmitted to the output display means 8, where the voice module 34 vocally indicates the testing result information. Also, the testing result and the related information are sent to the remote server 14 in the wireless network system 13, 14 via the wireless communication module 12 for data management and information consultation feedback.

3. The Making and Storing of the Standard Curve for the Test Substance

Various standard curves for the test substance may be stored on the electronic tag, and the standard curves include, but are not limited to, one of a correspondence curve between the series concentration of the standard product of the detected substance and $OD_{test\ line}/OD_{control\ line}$ and a correspondence curve between the series concentration of the standard product of the detected substance and $OD_{test\ line}/(OD_{test\ line}+OD_{control\ line})$. Herein, $OD_{test\ line}$ denotes the optical density value of the test line detected for the series concentration of the standard product of the detected substance, and $OD_{control\ line}$ denotes the optical density value of the control line detected for the series concentration of the standard product of the detected substance.

The method for making the standard curve includes:

1) Preparing the series concentrations of a standard product of the detected substance;

2) detecting the corresponding $OD_{test\ line}$ and $OD_{control\ line}$ for the series concentration of the standard product of the detected substance, thereby calculating the ratio of $OD_{test\ line}/OD_{control\ line}$ or the ratio of $OD_{test\ line}/(OD_{test\ line}+OD_{control\ line})$;

3) making a standard curve by taking the series concentration of the standard product as an X axis and taking the ratio of $OD_{test\ line}/OD_{control\ line}$ as a Y axis; or, drawing a standard curve by taking the series concentration of the standard product as the X axis and taking the ratio of $OD_{test\ line}/(OD_{test\ line}+OD_{control\ line})$ as the Y axis;

4) establishing a standard curve software, and storing the established software on the electronic tag 20; and 5) storing the optical density value ($OD_{control\ line}$) for the test strip control line obtained when making the standard curve and the corresponding numerical value of the characteristic wavelength of the excited light and/or the numerical value of the characteristic wavelength of the reflected light that are used during detection, together with the standard curve, on the electronic tag 20; during the practical detection of a sample, the optical density value ($OD_{control\ line}$) for the line test strip control line stored on the electronic tag 20 functions to monitor the success or failure of the test strip reaction (here, the reference optical density value for the test strip control line is represented by $OD_{control\ line'}$), and if the test strip reaction fails, a great statistic error may exist between the $OD_{control\ line}$ obtained during the sample test and the corresponding reference optical density value $OD_{control\ line'}$ stored on the electronic tag 20; here, the parameters stored on the electronic tag are matched with the test strip products of the same batch.

4. Testing Method for the Test Strip Testing System

A testing method for the test strip testing system is realized by the following steps of:

1) powering on the test strip testing system;

2) inserting the test strip 15 into the test strip card 1, and then inserting the test strip card 1 inserted with the test strip into the test strip card receptacle 33 of the testing device 2 of the test strip testing system;

3) dipping the sample absorption end of the test strip into a sample;

4) pressing a detection key of the system to start the sample test by the test strip testing system, and after the sample test is completed, the output display means 8 displays the test strip testing result and the relevant information, and at the same time, the voice module 34 vocally indicates the testing result information; and 5) pressing a sending key of the system, to send the testing result and the relevant information to the remote server 14 for data management and information consultation feedback.

Embodiment 3

Detection of Blood Serum Tumour Markers AFP, CEA and PSA Via the Test Strip Testing System Inserted with a Quantum Dot-Marked Test Strip (Single Detection for a Plurality of Components)

1. Manufacturing of a Quantum Dot-Marked Test Strip

The quantum dot-marked test strip 15 includes a sample pad 21, a glass fiber membrane binding pad 22, an analysis membrane 23 with a test line 27 and a control line 28, a super-absorbent pad 24 and a test strip reaction end position indication label 25, which are arranged sequentially and stuck mutually. The glass fiber membrane binding pad 22 is coated with a mixture of quantum dot-marked alphafetoprotein (AFP) monoclonal antibody, quantum dot-marked carcinoembryonic antigen (CEA) monoclonal antibody and quantum dot-marked prostate-specific antigen (PSA) monoclonal antibody; the test line 27 is coated with a mixture of AFP antibody, CEA antibody and PSA antibody; and the control line 28 is coated with a secondary antibody quality control substance, for example, goat anti-mouse IgM antibody, or goat anti-mouse IgG antibody, or rabbit anti-mouse IgM antibody, or rabbit anti-mouse IgG antibody.

1) Preparing the Components of the Test Strip i) the sample pad 21 is prepared in such a way that: a cellulose membrane is prepared and cut into membrane blocks each with a size of 297 mm×15 mm, which are then put into an elongated tank, then a sample pad treating liquid (i.e. pH=7.2 0.03 mol/L phosphate buffer+5% BSA+0.1%

Tween 20) is added to the elongated tank, and the membrane blocks are soaked at room temperature for 30 minutes. Then, the membrane blocks are taken out and dried sufficiently at 37° C.

ii) the glass fiber membrane binding pad 22 is prepared as follows: a glass fiber membrane is cut into membrane blocks each with a size of 297 mm×10 mm, which are put into an elongated tank, then a pre-prepared quantum dot marker solution (i.e. a mixture solution containing quantum dot-marked AFP monoclonal antibody, quantum dot-marked CEA monoclonal antibody and quantum dot-marked PSA monoclonal antibody) is added to the tank; then, the membrane blocks are taken out and dried sufficiently at 37° C.

iii) the analysis membrane 23 is prepared as follows: a cellulose nitrate membrane is cut into membrane blocks each with a size of 297 mm×25 mm, which are put into an elongated tank, then a mixture of AFP antibody (0.5-5 mg/ml), CEA antibody (0.5-5 mg/ml) and PSA antibody (0.5-5 mg/ml) is applied on the membrane blocks by a membrane dotter from bottom to top at a distance interval starting from the bottom margin of the membrane to form test lines 27, and a 0.5-5 mg/ml goat anti-mouse IgM antibody, or goat anti-mouse IgG antibody, or rabbit anti-mouse IgM antibody, or rabbit anti-mouse IgG antibody is applied on the membrane blocks by a membrane dotter to form control lines 28; and then the membrane blocks are sufficiently dried at 37° C.

iv) the super-absorbent pad 24 is prepared as follows: a cellulose membrane with a super-absorbent capability is cut into membrane blocks each with a size of 97 mm×30 mm, which are then dried sufficiently.

v) the test strip reaction end position indication label 25 is prepared as follows: a fine pH indicator paper with a detectable pH value range from 5.0 to 9.0 is cut into membrane blocks each with a size of 297 mm×5 mm, which are then dried sufficiently.

2) Assembling the Test Strip

The prepared components of the test strip, including the sample pad 21, the glass fiber membrane binding pad 22, the analysis membrane 23, the super-absorbent pad 24 and the test strip reaction end position indication label 25 are sequentially overlapped with one another and stuck on a plastic substrate 26, and the resultant product is cut into test strips of a certain size. The test strips are respectively packaged in test strip boxes and maintained in a dry condition.

2. Making and Storing a Standard Curve

Figure 9:
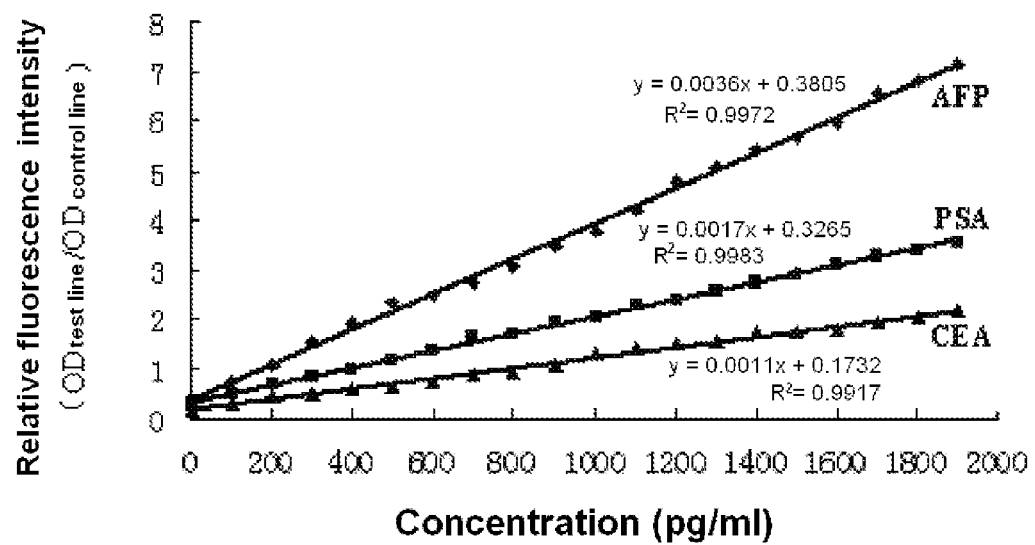
FIG. 9 shows standard curves for the detection of tumour markers AFP, CEA and PSA.

FIG. 9 shows the standard curves for the detection of AFP, CEA and PSA, and a method for making these standard curves is as follows:

1) Preparing a Standard Product Series Concentration 20 series concentrations of 0 pg/ml, 100 pg/ml, 200 pg/ml, 300 pg/ml, 400 pg/ml, 500 pg/ml, 600 pg/ml, 700 pg/ml, 800 pg/ml, 900 pg/ml, 1000 pg/ml, 1100 pg/ml, 1200 pg/ml, 1300 pg/ml, 1400 pg/ml, 1500 pg/ml, 1600 pg/ml, 1700 pg/ml, 1800 pg/ml, 1900 pg/ml of each of AFP, CEA and PSA standard products are prepared by employing 1:10 diluted normal human blood serum (which is diluted by a pH=7.2 0.03 mol/L PB buffer) as a diluent.

2) Making a Standard Curve for the Detection of a Tumour Marker

The tumour marker standard product of each of the series concentrations is tested by 10 quantum dot-marked tumour marker test strips (which is suitable for testing a plurality of components) for ten times under the same conditions, the test line optical density value ($OD_{test\ line}$) and the control line optical density value ($OD_{control\ line}$) of each of the test strips are read, and an average value and a ratio of $OD_{test\ line}/OD_{control\ line}$ are obtained, so that a standard curve is drawn by taking the series concentration of the tumour marker standard product as the X axis and taking the ratio of $OD_{test\ line}/OD_{control\ line}$ corresponding to the series concentration of the tumour marker standard product as the Y axis, as shown in FIG. 9.

3) establishing a standard curve software for tumour marker detection, and storing the standard curve software, together with the $OD_{control\ line}$ value (which is taken as the reference optical density value $OD_{control\ line'}$ of the test strip control line during the practical detection of a sample) and the corresponding numerical value of the characteristic wavelength of the excited light and numerical value of the characteristic wavelength of the reflected light used during the detection of AFP, CEA and PSA standard products, on the electronic tag 20.

3. Tumour Marker Detection of a Blood Serum Sample from a Tumour Patient

1) Sample Source: The blood serum sample is provided by a control laboratory of a certain tumour hospital. Before detection, the blood serum sample is 10-fold (i.e. 1:10) diluted by a pH=7.2 0.03 mol/L PB buffer.

2) Sample Test i) powering on the test strip testing system;

ii) inserting the test strip 15 into the test strip card 1, and then inserting the test strip card 1 inserted with the test strip into the test strip card receptacle 33 of the testing device 2 of the test strip testing system;

iii) dipping the sample absorption end of the test strip into a sample;

iv) pressing a detection key of the system to start the sample test by the test strip testing system, and after the sample test is completed, the output display means 8 displays the test strip testing result and the relevant information, and at the same time, the voice module 34 vocally indicates the testing result information; and v) pressing a sending key of the system, to send the testing result and the relevant information to the remote server 14 for data management and information consultation feedback.

Figure 10:
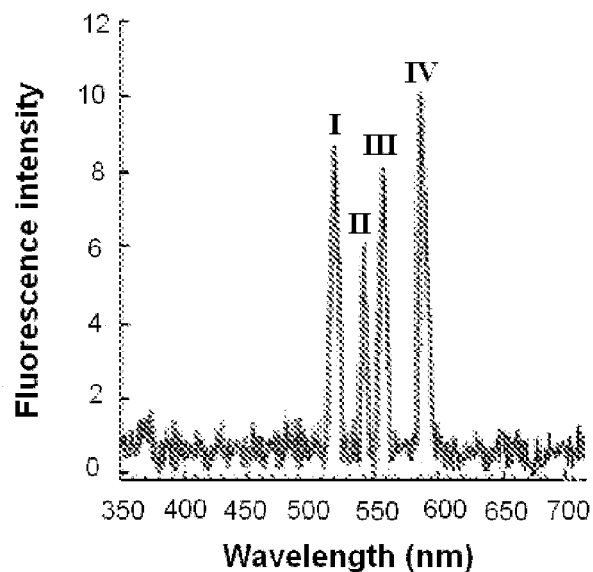
FIG. 10 shows a fluorescence spectrum curve of quantum dot-marked AFP, CEA and PSA.

3) Calculation of Final AFP, CEA and PSA Concentrations in a Blood Serum Sample from a Tumour Patient The calculation of final AFP, CEA and PSA concentrations in a blood serum sample is conducted by a formula: final tumour marker concentration of a blood serum sample (pg/ml)=concentration detected by the test strip testing system×blood serum dilution fold For example: the detection of a blood serum sample by the test strip testing system obtain that the AFP concentration thereof is 1753.4526 pg/ml, the CEA concentration is 878.3892 pg/ml, and the PSA concentration is 983.4257 pg/ml, then:

final AFP concentration of the blood serum sample (pg/ml)=1753.4526 pg/ml×10=17534.526 pg/ml final CEA concentration of the blood serum sample (pg/ml)=878.3892 pg/ml×10=8783.892 pg/ml final PSA concentration of the blood serum sample (pg/ml)=983.4257 pg/ml×10=9834.257 pg/ml FIG. 10 shows a fluorescence spectrum curve of quantum dot-marked AFP, CEA and PSA, where, I represents the AFP spectrum peak in the test line, II represents the CEA spectrum peak in the test line, III represents the PSA spectrum peak in the test line, and the IV represents the quality control substance spectrum peak in the control line.

Embodiment 4

Detection of Hepatitis B Surface Antigen HBsAg by the Test Strip Testing System Inserted with a Colloidal Gold-Marked Test Strip (Monocomponent Detection)

1. Manufacturing of Colloidal Gold-Marked HBsAg Test Strip

The colloidal gold-marked HBsAg test strip includes a sample pad 21, a glass fiber membrane binding pad 22 coated with colloidal gold-marked HBsAg monoclonal antibody, an analysis membrane 23 with a test line 27 and a control line 28, a super-absorbent pad 24 and a test strip reaction end position indication label 25, which are sequentially overlapped with one another and stuck mutually. The test line 27 is coated with HBsAg antibody. The control line 28 is coated with a secondary antibody quality control substance, for example, goat anti-mouse IgM antibody, or goat anti-mouse IgG antibody, or rabbit anti-mouse IgM antibody, or rabbit anti-mouse IgG antibody.

1) Preparing the Components of the Test Strip i) the sample pad 21 is prepared in such a way that: a cellulose membrane is prepared and cut into membrane blocks each with a size of 297 mm×15 mm, which are then put into an elongated tank, then a sample pad treating liquid (i.e. pH=7.2 0.03 mol/Lphosphate buffer+5% BSA+0.1% Tween 20) is added to the tank, and the membrane blocks are soaked at room temperature for 30 minutes. Then, the membrane blocks are taken out and dried sufficiently at 37° C.

ii) the glass fiber membrane binding pad 22 is prepared as follows: a glass fiber membrane is cut into membrane blocks each with a size of 297 mm×10 mm, which are put into an elongated tank, then a conjugate solution of colloidal gold-marked HBsAg monoclonal antibody is added to the tank, and then the membrane blocks are taken out and dried sufficiently at 37° C.

iii) the analysis membrane 23 is prepared as follows: a cellulose nitrate membrane is cut into membrane blocks each with a size of 297 mm×25 mm, which are put into an elongated tank, then a 0.5-5 mg/ml HBsAg antibody is applied on the membrane blocks by a membrane dotter at a distance interval from bottom to top starting from the bottom margin of the membrane to form test lines 27, and a 0.5-5 mg/ml goat anti-mouse IgM antibody, or goat anti-mouse IgG antibody, or rabbit anti-mouse IgM antibody, or rabbit anti-mouse IgG antibody is applied to form control lines 28, and then the membrane blocks are sufficiently dried at 37° C.

iv) the super-absorbent pad 24 is prepared as follows: a cellulose membrane with a super-absorbent capability is cut into membrane blocks each with a size of 297 mm×30 mm, which are then dried sufficiently.

v) the test strip reaction end position indication label 25 is prepared as follows: a fine pH indicator paper with a detectable pH value range from 5.0 to 9.0 is cut into membrane blocks each with a size of 297 mm×5 mm, which are then dried sufficiently.

2) Assembling the Test Strip

The prepared components for the test strip, including the sample pad 21, the glass fiber membrane binding pad 22, the analysis membrane 23, the super-absorbent pad 24 and the test strip reaction end position indication label 25, are sequentially overlapped with one another and stuck on a plastic substrate 26, and the resultant product is cut into test strips of a certain size. The test strips are respectively packaged in test strip boxes and maintained in a dry condition.

2. Making and Storing a Standard Curve for the Detection of Hepatitis B Surface Antigen HBsAg FIG. 11 shows a standard curve for HBsAg detection, and a method for making the standard curve is as follows:

1) Preparing Series Concentrations of an HBsAg Standard Product 20 series concentrations of 0 pg/ml, 100 pg/ml, 200 pg/ml, 300 pg/ml, 400 pg/ml, 500 pg/ml, 600 pg/ml, 700 pg/ml, 800 pg/ml, 900 pg/ml, 1000 pg/ml, 1100 pg/ml, 1200 pg/ml, 1300 pg/ml, 1400 pg/ml, 1500 pg/ml, 1600 pg/ml, 1700 pg/ml, 1800 pg/ml, 1900 pg/ml of the HBsAg standard product are prepared by employing 1:10 diluted normal human blood serum (which is diluted by a pH=7.2 0.03 mol/L PB buffer) as a diluent.

2) Making a Standard Curve for the Detection of HBsAg

Figure 11:
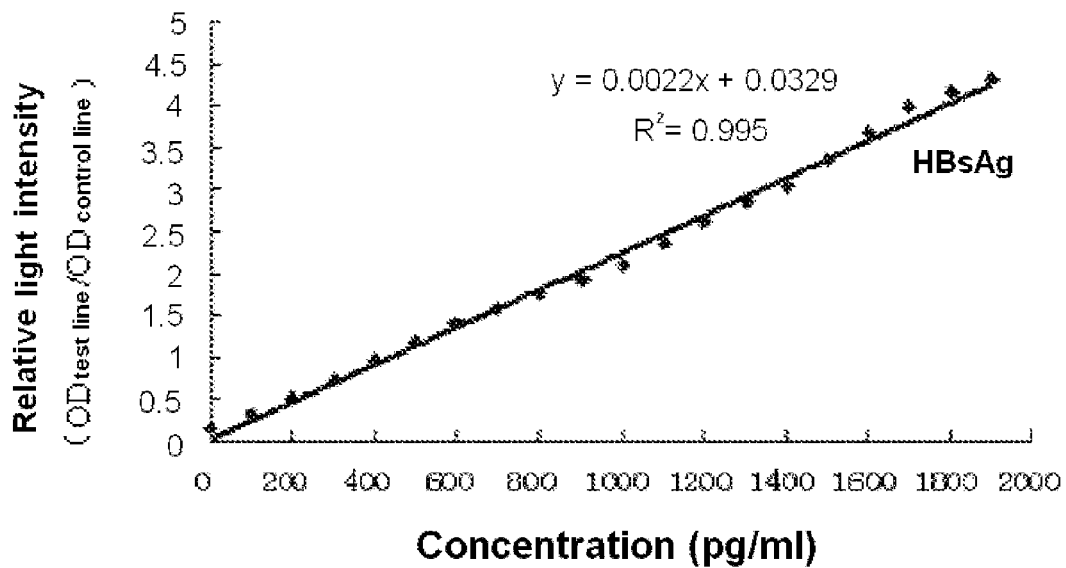
FIG. 11 shows a standard curve for the detection of a hepatitis B surface antigen (HBsAg)

The HBsAg standard product of each of the above series concentrations is tested by 10 colloidal gold-marked HBsAg test strips for ten times under the same conditions, the test line optical density value ($OD_{test\ line}$) and the control line optical density value ($OD_{control\ line}$) of each of the test strips are read, and an average value and a ratio of $OD_{test\ line}/OD_{control\ line}$ are calculated, so that a standard curve is drawn by taking the series concentrations of the HBsAg standard product as the X axis and taking the ratio of $OD_{test\ line}/OD_{control\ line}$ corresponding to the series concentration of the HBsAg standard product as the Y axis, as shown in FIG. 11.

3) establishing a standard curve software for HBsAg detection, and storing the standard curve software, together with the $OD_{control\ line}$ value (which is taken as the reference optical density value $OD_{control\ line'}$ of the test strip control line during the practical detection of a sample) and the numerical value of the characteristic wavelength of the excited light and the numerical value of the characteristic wavelength of the reflected light used during the detection of the HBsAg standard products, on the electronic tag 20.

3. Detection of HBsAg in a Blood Serum Sample from a Hepatitis B Patient

1) Sample Source: the blood serum sample from a hepatitis B patient is provided by a certain mother and child health care center, and the blood serum sample is 10-fold (i.e. 1:10) diluted by a pH=7.2 0.03 mol/L PB buffer before detection.

2) Sample Test:

i) powering on the test strip testing system;

ii) inserting the test strip 15 into the test strip card 1, and then inserting the test strip card 1 inserted with the test strip into the test strip card receptacle 33 of the testing device 2 of the test strip testing system;

iii) dipping the sample absorption end of the test strip into a sample;

iv) pressing a detection key of the system to start the sample test by the test strip testing system, and after the sample test is completed, the output display means 8 displays the test strip testing result and the relevant information, and at the same time, the voice module 34 vocally indicates the testing result information; and v) pressing a sending key of the system, to send the testing result and the relevant information to the remote server 14 for data management and information consultation feedback.

3) Calculation of Final HBsAg Concentration of the Blood Serum Sample from a Hepatitis B Patient:

Final HBsAg concentration (pg/ml) in the blood serum sample=HBsAg concentration detected by the test strip testing system×dilution fold of blood serum.

For example, the detection of a blood serum sample by the test strip testing system obtains that the HBsAg concentration of the blood serum sample is 205.9563 pg/ml, thus:

final HBsAg concentration (pg/ml) of the blood serum sample=205.9563 pg/ml×10=2059.563 pg/ml.

Figure 12:
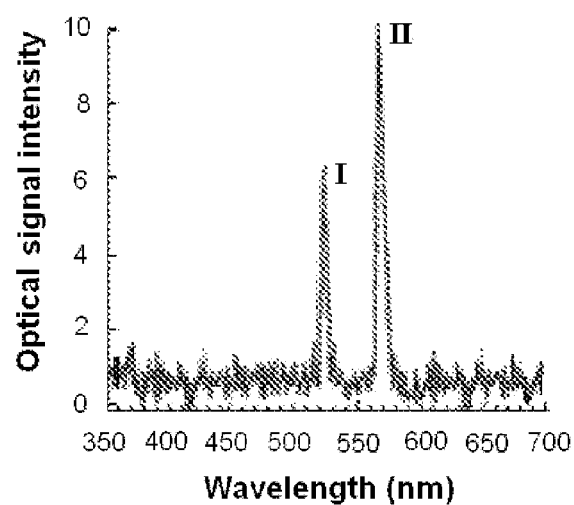
FIG. 12 shows a spectral curve of colloidal gold-marked HBsAg.

FIG. 12 shows a spectral curve of colloidal gold-marked HBsAg, wherein, I represents the HBsAg spectrum peak in the test line, and II represents the quality control substance spectrum peak in the control line.

Embodiment 5

Detection of Blood Serum Carcinoembryonic Antigen CEA by the Test Strip Testing System Inserted with a Nano Rare Earth Fluorescent Complex-Marked Test Strip (Monocomponent Detection)

For example, $Eu^{3+}$ nano microparticle is used as the nano rare earth fluorescent complex.

A $Eu^{3+}$ nano microparticle-marked test strip includes a sample pad 21, a glass fiber membrane binding pad 22, an analysis membrane 23 with a test line 27 and a control line 28, a super-absorbent pad 24 and a test strip reaction end position indication label 25, which are sequentially overlapped with one another and stuck mutually. The glass fiber membrane binding pad 22 is coated with $Eu^{3+}$ nano microparticle-marked CEA monoclonal antibody; the test line 27 is coated with CEA antibody; and the control line 28 is coated with a secondary antibody quality control substance, for example, goat anti-mouse IgM antibody, or goat anti-mouse IgG antibody, or rabbit anti-mouse IgM antibody, or rabbit anti-mouse IgG antibody.

1) Preparing the Components of the Test Strip i) the sample pad 21 is prepared in such a way that: a cellulose membrane is selected and cut into membrane blocks each with a size of 297 mm×15 mm, which are then put into an elongated tank, then a sample pad treating liquid (i.e. pH=7.2 0.03 mol/L phosphate buffer+5% BSA+0.1% Tween 20) is added to the elongated tank, and the membrane blocks are soaked at room temperature for 30 minutes. Then, the membrane blocks are taken out and dried sufficiently at 37° C.

ii) the glass fiber membrane binding pad 22 is prepared as follows: a glass fiber membrane is cut into membrane blocks each with a size of 297 mm×10 mm, which are put into an elongated tank, then a pre-prepared $Eu^{3+}$ nano microparticle-marked CEA monoclonal antibody solution is added to the tank, and then the membrane blocks are taken out and dried sufficiently at 37° C.

iii) the analysis membrane 23 is prepared as follows: a cellulose nitrate membrane is cut into membrane blocks each with a size of 297 mm×25 mm, which are put into an elongated tank, then a 0.5-5 mg/ml CEA antibody is applied on the membrane blocks by a membrane dotter at a distance interval from bottom to top starting from the bottom margin of the membrane to form test lines 27, and a 0.5-5 mg/ml goat anti-mouse IgM antibody, or goat anti-mouse IgG antibody, or rabbit anti-mouse IgM antibody, or rabbit anti-mouse IgG antibody is applied on the membrane blocks by a membrane dotter to form control lines 28, and then the membrane blocks are sufficiently dried at 37° C.

iv) the super-absorbent pad 24 is prepared as follows: a cellulose membrane with a super-absorbent capability is cut into membrane blocks each with a size of 297 mm×30 mm, which are then dried sufficiently.

v) the test strip reaction end position indication label 25 is prepared as follows: a fine pH indicator paper with a detectable pH value range from 5.0 to 9.0 is cut into membrane blocks each with a size of 297 mm×5 mm, which are then dried sufficiently.

2) Assembling the Test Strip

The prepared components for the test strip, including the sample pad 21, the glass fiber membrane binding pad 22, the analysis membrane 23, the super-absorbent pad 24 and the test strip reaction end position indication label 25, are sequentially overlapped with one another and stuck on a plastic substrate 26, and the resultant product is cut into test strips of a certain size. The test strips are respectively packaged in test strip boxes and maintained in a dry condition.

2. Making and Storing a Standard Curve

Figure 13:
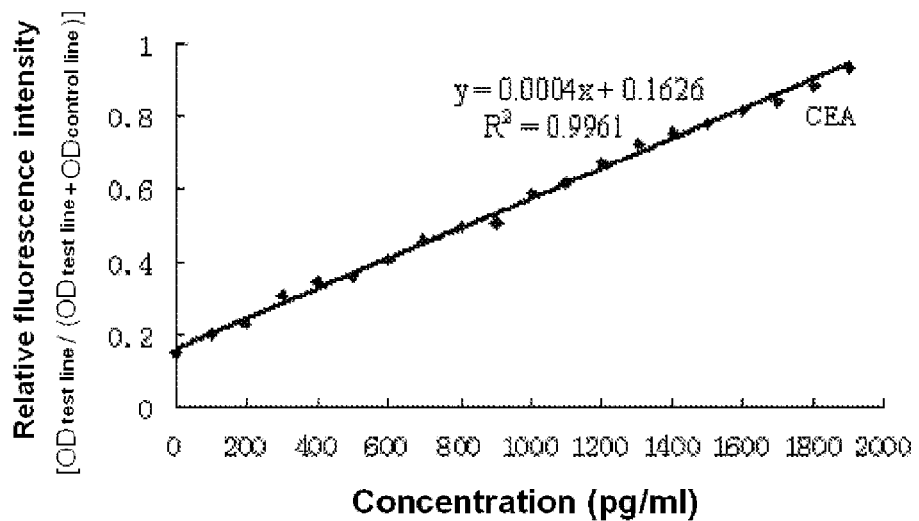
FIG. 13 shows a standard curve for the detection of carcinoembryonic antigen CEA.

FIG. 13 shows a standard curve for the detection of carcinoembryonic antigen CEA, and a method for making the standard curve is as follows:

1) Preparing Standard Product Series Concentrations 20 series concentrations of 0 pg/ml, 100 pg/ml, 200 pg/ml, 300 pg/ml, 400 pg/ml, 500 pg/ml, 600 pg/ml, 700 pg/ml, 800 pg/ml, 900 pg/ml, 1000 pg/ml, 1100 pg/ml, 1200 pg/ml, 1300 pg/ml, 1400 pg/ml, 1500 pg/ml, 1600 pg/ml, 1700 pg/ml, 1800 pg/ml, 1900 pg/ml of the CEA standard product are prepared by employing 1:10 diluted normal human blood serum (which is diluted by a pH=7.2 0.03 mol/L PB buffer) as a diluent.

2) Making a Standard Curve for the Detection of CEA

The CEA standard product of each of the series concentrations is tested by 10 $Eu^{3+}$ nano microparticle-marked CEA test strips under the same conditions for ten times, the test line optical density value ($OD_{test\ line}$) and the control line optical density value ($OD_{control\ line}$) of each of the test strips are read respectively, and an average value and a ration of $OD_{test\ line}/(OD_{test\ line}+OD_{control\ line})$ are obtained, so that a standard curve is drawn by taking the series concentration of the CEA standard product as the X axis and taking the ratio of $OD_{test\ line}/(OD_{test\ line}+OD_{control\ line})$ corresponding to the series concentration of the CEA standard product as the Y axis, as shown in FIG. 13.

3) establishing a standard curve software for CEA detection, and storing the standard curve software, together with the $OD_{control\ line}$ value (which is taken as the reference optical density value $OD_{control\ line'}$ of the test strip control line during the practical detection of a sample) and the numerical value of the characteristic wavelength of the excited light and the numerical value of the characteristic wavelength of the reflected light used during the detection of CEA standard products, on the electronic tag 20.

3. Detection of CEA in a Blood Serum Sample

1) Sample Source: the blood serum sample is provided by a control laboratory of a certain mother and child health care center, and the blood serum sample is 10-fold (i.e. 1:10) diluted by a pH=7.2 0.03 mol/L PB buffer before detection.

2) Sample Test:

i) powering on the test strip testing system;

ii) inserting the test strip 15 into the test strip card 1, and then inserting the test strip card 1 inserted with the test strip into the test strip card receptacle 33 of the testing device 2 of the test strip testing system;

iii) dipping the sample absorption end of the test strip into a sample;

iv) pressing a detection key of the system to start the sample test by the test strip testing system, and after the sample test is completed, the output display means 8 displays the test strip testing result and the relevant information, and at the same time, the voice module 34 vocally indicates the testing result information; and v) pressing a sending key of the system, to send the testing result and the relevant information to the remote server 14 for data management and information consultation feedback.

Figure 14:
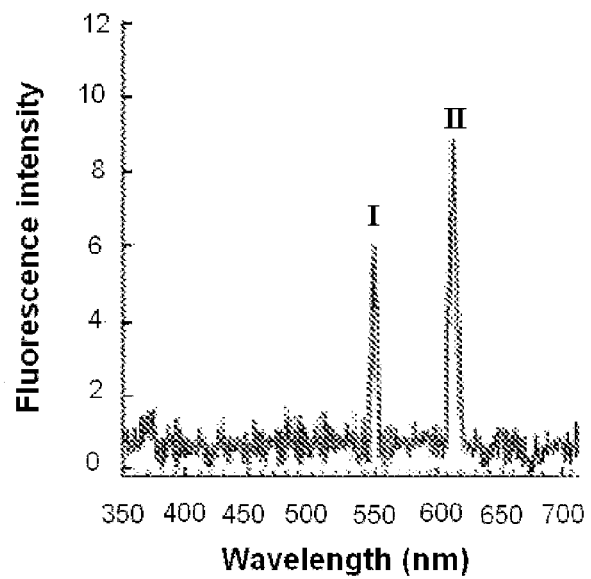
FIG. 14 shows a fluorescence spectrum curve of $Eu^{3+}$ nano microparticle-marked CEA.

3) Calculation of Final CEA Concentration of a Blood Serum Sample final CEA concentration (pg/ml) in the blood serum sample=CEA concentration detected by the test strip testing system×dilution fold of blood serum For example: the detection of a blood serum sample by the test strip testing system obtains that the CEA concentration of the blood serum sample is 586.4602 pg/ml, then:

final CEA concentration (pg/ml) of the blood serum sample=586.4602 pg/ml×10=5864.602 pg/ml FIG. 14 shows a fluorescence spectrum curve of $Eu^{3+}$ nano microparticle-marked CEA, where, I represents the CEA spectrum peak in the test line, and II represents the quality control substance spectrum peak in the control line.

Figure 15:
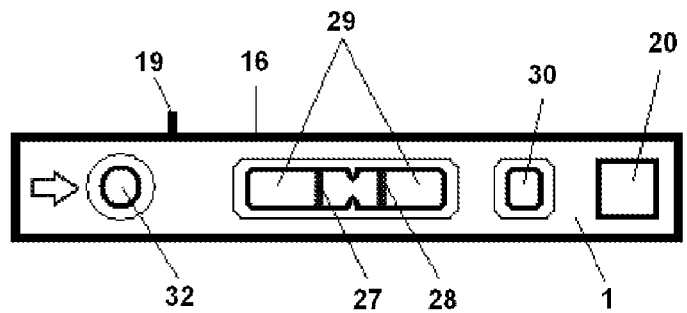
FIG. 15 is a top view showing the structure of another scheme of the test strip card.

The above Embodiments and the drawings thereof are only used to further illustrate the invention, rather than to limit the protection scope of the invention thereto. It should be noted that other modifications may be further made to the test strip testing system according to the invention, for example, the test line 27 on the analysis membrane 23 of the test strip may be a plurality of test lines or a plurality of test points; or the test strip may be set with no control line; the left end of the test strip card 1 may also be sealed so as to install the test strip in the test strip card box for detection, and in such a case, the test strip card 1 is usually set with a sample application hole 32 for the application of a sample on the upper side of the card box 16 corresponding to the sample pad 21 of the test strip (as shown in FIG. 15); in addition to being installed on the test strip card box 16, the electronic tag 20 on which a standard curve of an object to be detected is stored may also be directly installed on the test strip 15 in the card box; the test strip 15 inserted into the card box may also be replaced with a biochip (including antibody chip, albumen chip, DNA chip and microfluidic chip) and the like. Therefore, all other technical solutions, which are obtained from any equivalent substitutions or equivalent variations of the test strip testing system according to the invention, fall into the protection scope of the invention as defined by the appended claims.

What is claimed is:

1. A test strip testing system, comprising a test strip card and a testing device, wherein the test strip card comprises a test strip card box, a test strip inserted into the test strip card box, and an electronic tag that is installed on the test strip card box and configured to store test strip information; and the testing device comprises an optical system, a photoelectric detector, an analog-to-digital converter, a data processor, an electronic tag reading and writing module with an antenna, a cell box, an output display means and a plurality of keys located on a surface of the testing device, wherein an imaging signal terminal of the optical system is connected with the photoelectric detector, a signal output terminal of the photoelectric detector is connected with a signal input terminal of the analog-to-digital converter via a signal amplifier, a signal output terminal of the analog-to-digital converter is connected with a signal input terminal of the data processor, and the data processor is further connected with the cell box, the output display means, the plurality of keys on the surface of the testing device and the electronic tag reading and writing module with an antenna; and the cell box is configured to receive a power supply which supplies power to the optical system, the photoelectric detector, the analog-to-digital converter and the electronic tag reading and writing module with an antenna via the data processor, wherein the test strip card is configured to be inserted into the testing device;

the test strip is configured to be inserted into the test strip card;

a front end of the testing device is provided with a test strip card receptacle, which is configured to receive the test strip card inserted with a test strip, for testing a sample on the test strip;

the test strip card box of the test strip card has an opening end for receiving the test strip as desired during sample test, an upper side of the opening end of the test strip card box has a notch for easily inserting the test strip into the test strip card box, a sample absorption end of the test strip that is inserted into the card box extends out of the opening end of the test strip card box to allow the test strip to dip into and absorb the sample, the upper side of the test strip card box is provided with a verification window at a location corresponding to a test line and a control line of the test strip in the card box and is provided with a test strip reaction end position observation window at a location corresponding to a test strip reaction end position indication label of the test strip in the card box, and a test strip card insertion stop flag is provided on the surface of the test strip card at a location corresponding to the test strip card receptacle of the testing device;

the electronic tag is configured to store a standard curve for a substance to be detected that is used for quantifying a sample concentration by test strips of the same batch or to store both a standard curve for a substance to be detected that is used for quantifying a sample concentration by test strips of the same batch and a reference optical density value ($OD_{control\ line'}$) of the test strip control line, and store a numerical value of a characteristic wavelength of excited light and/or reflected light for detection of the substance to be detected, wherein the electronic tag is installed at any location of the test strip card box;

the testing device further comprises a voice module which is connected with the data processor;

light emitted by the optical system is configured to excite reaction signifiers of the test line and the control line of the test strip to emit reflected light, which is then received and converted into an electrical signal by the photoelectric detector, and the electrical signal is amplified and transmitted to the analog-to-digital converter to be converted into a digital signal, which is then transmitted to the data processor, wherein the data processor is configured to automatically identify the received digital signal representing an optical signal with the characteristic frequency, calculate the concentration of the detected substance and perform technical analysis according to the standard curve of the detected substance stored on the test strip card electronic tag that is transmitted by the electronic tag reading and writing module, and transmit a testing result to the output display means, and the voice module is configured to vocally indicate the testing result information.

2. The test strip testing system according to claim 1, wherein the electronic tag of the test strip card is configured to store the standard curve of a diversified form which comprises one of:
   a correspondence curve between series concentrations of a standard product of the detected substance and $OD_{test\ line}/OD_{control\ line}$; or
   a correspondence curve between series concentrations of the standard product of the detected substance and $OD_{test\ line}/(OD_{test\ line}+OD_{control\ line})$;
   wherein, $OD_{test\ line}$ denotes an optical density value of the test line detected for the series concentrations of the standard product of the detected substance, and $OD_{control\ line}$ denotes the optical density value of the control line detected for the series concentrations of the standard product of the detected substance.

3. The test strip testing system according to claim 1, wherein the electronic tag of the test strip card is an RFID tag or a non-contact identification IC card.

4. The test strip testing system according to claim 1, wherein the test strip inserted into the test strip card is any one from a group comprising: quantum dot-marked test strip, colloidal gold-marked test strip, colloidal selenium-marked test strip, upconversion phosphorescence-marked test strip, nano rare earth fluorescent complex-marked test strip, temporal resolution chromatography test strip and chemiluminescence test strip.

5. The test strip testing system according to claim 1, wherein the test strip information stored on the electronic tag further comprises a test strip batch number, test strip expiration date, electronic tag cryptogram, a reference value of a clinical index, and test strip manufacturer information, and identity information of a tested object, tester cryptogram, a sample name, a sample sequence number, test date and a test result are writable into the electronic tag.

6. The test strip testing system according to claim 1, wherein the test strip inserted into the test strip card is disposable; the card box of the test strip card for receiving the test strip and the electronic tag installed on the card box are matched with test strips of the same batch; and the testing device is a durable general-purpose product.

7. The test strip testing system according to claim 1, wherein the testing device is in general a portable instrument, a medium or large sized instrument, or a combination with a wireless communication product that has the corresponding information transmitting and receiving functions, including a combination with one selected from a group consisted of: a mobile phone, a tablet computer, a personal digital assistant, a mobile terminal equipment and a computer.

8. The test strip testing system according to claim 1, wherein the card box of the test strip card is made of a thin rigid plastic material or rigid paper material.

9. The test strip testing system according to claim 1, wherein the optical system has such a structure that:
   a) the optical system comprises an illuminating system and an imaging system, wherein the illuminating system includes an exciting light source, and an optical fiber bundle, a collimating lens, a dichroic mirror, a front lens group form an output light path from the light source to the test strip card; the imaging system comprises a front lens group, a dichroic mirror, a filter plate and a rear lens group that are arranged coaxially, wherein an included angle of 45° is formed between a reflecting surface of the dichroic mirror and the optical axis, the front lens group and the rear lens group both employ an isolated structure, a light path of the illuminating system before the dichroic mirror is vertical to the optical axis of the imaging system, and a light path of the illuminating system after the dichroic mirror is coaxial with the imaging system; the photoelectric detector is located on an image plane of the rear lens group; the optical fiber bundle is configured to divide the light emitted by the light source into two laser beams with the same intensity that are spaced apart from each other, and these two laser beams are collimated by the collimating lens into two parallel light beams which irradiate on the surface of the dichroic mirror, and synchronously irradiate on the test line and the control line of the test strip in the test strip card that are located in an object plane of the front lens group via the front lens group after being reflected by the dichroic mirror, to excite the test strip reaction signifier that permeates to the test line and the control line to emit reflected light with a characteristic frequency, the reflected light from the test line and the control line passes through the same front lens group and the dichroic mirror, is filtered by the filter plate to filter out parasitic light, exits from the rear lens group, and then enters into the photoelectric detector to be detected and converted into an electrical signal by the photoelectric detector; or
   b) the optical system comprises an exciting light source, and an incident light coupler, incident light optical fibers, optical fiber probes, emergent light optical fibers and emergent light couplers form an output light path from the exciting light source to the photoelectric detector; the light emitted by the light source is divided into two light beams by the incident light coupler, and these two light beams respectively enter the incident light optical fibers, and then respectively irradiate on the test line and the control line of the test strip in the test strip card via the optical fiber probe for the test line of the test strip and the optical fiber probe for the control line of the test strip, to excite the reaction signifiers of the test line and the control line of the test strip to emit reflected light beams with the characteristic frequency, and the reflected light beams respectively pass through the optical fiber probe for the test line and the optical fiber probe for the control line, the corresponding emergent light optical fibers and the emergent light couplers, and then enter the photoelectric detector to be detected and converted into an electrical signal by the photoelectric detector; each of the optical fiber probes has a bundling and sharing structure, that is, an inner part of the optical fiber probe for the test line functions as the incident light optical fiber, and an outer part of the optical fiber probe functions as the emergent light optical fiber; while an inner part of the optical fiber probe for the control line functions as the incident light optical fiber, and an outer part of the optical fiber probe functions as the emergent light optical fiber.

10. The test strip testing system according to claim 1, wherein
   the testing device of the test strip testing system further comprises a wireless communication module connected with the data processor, and the power supply in the cell box is configured to further supply power to the wireless communication module; and the test strip testing system further comprises a wireless network system, that is in communication with a signal transmission end of the wireless communication module and comprises a remote server;

the data processor is configured to automatically identify the optical signals with the characteristic frequency transmitted from the test line and the control line, calculate the concentration of the detected substance and perform technical analysis according to the standard curve of the detected substance stored on the test strip card electronic tag that is transmitted by the electronic tag reading and writing module, and transmit a testing result to the output display means, and the voice module is configured to vocally indicate the testing result information, wherein the testing result and the related information are further sent to the remote server of the wireless network system via the wireless communication module for data management and information consultation feedback.

11. The test strip testing system according to claim 10, wherein the electronic tag of the test strip card is configured to store the standard curve of a diversified form which comprises one of:

a correspondence curve between the series concentration of a standard product of the detected substance and $OD_{test\ line}/OD_{control\ line}$; or a correspondence curve between the series concentration of the standard product of the detected substance and $OD_{test\ line}/(OD_{test\ line}+OD_{control\ line})$;

wherein $OD_{test\ line}$ denotes the optical density value of the test line detected for the series concentration of the standard product of the detected substance, and $OD_{control\ line}$ denotes the optical density value of the control line detected for the series concentration of the standard product of the detected substance.

12. The test strip testing system according to claim 10, wherein the electronic tag of the test strip card is an RFID tag or a non-contact identification IC card.

13. The test strip testing system according to claim 10, wherein the test strip inserted into the test strip card is any one from a group comprising: quantum dot-marked test strip, colloidal gold-marked test strip, colloidal selenium-marked test strip, upconversion phosphorescence-marked test strip, nano rare earth fluorescent complex-marked test strip, temporal resolution chromatography test strip and chemiluminescence test strip.

14. The test strip testing system according to claim 10, wherein the test strip information stored on the electronic tag further comprises a test strip batch number, test strip expiration date, electronic tag cryptogram, a reference value of a clinical index, and test strip manufacturer information, and identity information of a tested object, tester cryptogram, a sample name, a sample sequence number, test date and a test result are writable into the electronic tag.

15. The test strip testing system according to claim 10, wherein the test strip inserted into the test strip card is disposable; the card box of the test strip card for receiving the test strip and the electronic tag installed on the card box are matched with test strips of the same batch; and the testing device is a durable general-purpose product.

16. The test strip testing system according to claim 10, wherein the testing device is in general a portable instrument, a medium or large sized instrument, or a combination with a wireless communication product that has the corresponding information transmitting and receiving functions, including a combination with one selected from a group consisted of: a mobile phone, a tablet computer, a personal digital assistant, a mobile terminal equipment and a computer.

17. The test strip testing system according to claim 10, wherein the card box of the test strip card is made of a thin rigid plastic material or rigid paper material.

18. The test strip testing system according to claim 10, wherein the optical system has such a structure that:

a) the optical system comprises an illuminating system and an imaging system, wherein the illuminating system includes an exciting light source, and an optical fiber bundle, a collimating lens, a dichroic mirror, a front lens group form an output light path from the light source to the test strip card; the imaging system comprises a front lens group, a dichroic mirror, a filter plate and a rear lens group that are arranged coaxially, wherein an included angle of 45° is formed between a reflecting surface of the dichroic mirror and the optical axis, the front lens group and the rear lens group both employ an isolated structure, a light path of the illuminating system before the dichroic mirror is vertical to the optical axis of the imaging system, and a light path of the illuminating system after the dichroic mirror is coaxial with the imaging system; the photoelectric detector is located on an image plane of the rear lens group; the optical fiber bundle is configured to divide the light emitted by the light source into two laser beams with the same intensity that are spaced apart from each other, and these two laser beams are collimated by the collimating lens into two parallel light beams which irradiate on the surface of the dichroic mirror, and synchronously irradiate on the test line and the control line of the test strip in the test strip card that are located in an object plane of the front lens group via the front lens group after being reflected by the dichroic mirror, to excite the test strip reaction signifier that permeates to the test line and the control line to emit reflected light with a characteristic frequency, the reflected light from the test line and the control line passes through the same front lens group and the dichroic mirror, is filtered by the filter plate to filter out parasitic light, exits from the rear lens group, and then enters into the photoelectric detector to be detected and converted into an electrical signal by the photoelectric detector; or b) the optical system comprises an exciting light source, and an incident light coupler, incident light optical fibers, optical fiber probes, emergent light optical fibers and emergent light couplers form an output light path from the exciting light source to the photoelectric detector; the light emitted by the light source is divided into two light beams by the incident light coupler, and these two light beams respectively enter the incident light optical fibers, and then respectively irradiate on the test line and the control line of the test strip in the test strip card via the optical fiber probe for the test line of the test strip and the optical fiber probe for the control line of the test strip, to excite the reaction signifiers of the test line and the control line of the test strip to emit reflected light beams with the characteristic frequency, and the reflected light beams respectively pass through the optical fiber probe for the test line and the optical fiber probe for the control line, the corresponding emergent light optical fibers and the emergent light couplers, and then enter the photoelectric detector to be detected and converted into an electrical signal by the photoelectric detector; each of the optical fiber probes has a bundling and sharing structure, that is, an inner part of the optical fiber probe for the test line functions as the incident light optical fiber, and an outer part of the optical fiber probe functions as the emergent light optical fiber; while an inner part of the optical fiber probe for the control line functions as the incident light optical fiber, and an outer part of the optical fiber probe functions as the emergent light optical fiber.

19. The test strip testing system according to claim 1, wherein the sample to be tested is any of liquid samples or viscous samples comprising clinical or non-clinical samples comprising blood, body fluid, urine, saliva, and genital secretion, wherein the clinical samples comprise a sample of infectious disease, hormone, cardiovascular disease, tumour, cancer, diabetes and autoimmune disease, and the non-clinical samples comprise a sample for food detection, environmental pollution detection, pesticide residue detection, biological contamination detection, biological agent detection, veterinary detection and drug detection.

20. The test strip testing system according to claim 10, wherein the sample to be tested is any of liquid samples or viscous samples comprising clinical or non-clinical samples comprising blood, body fluid, urine, saliva, and genital secretion, wherein the clinical samples comprise a sample of infectious disease, hormone, cardiovascular disease, tumour, cancer, diabetes and autoimmune disease, and the non-clinical samples comprise a sample for food detection, environmental pollution detection, pesticide residue detection, biological contamination detection, biological agent detection, veterinary detection and drug detection.

\* \* \* \* \*